(12) United States Patent
Kathirgamanathan et al.

(10) Patent No.: US 7,927,717 B2
(45) Date of Patent: Apr. 19, 2011

(54) ELECTROLUMINESCENT MATERIALS AND DEVICES

(75) Inventors: Poopathy Kathirgamanathan, North Harrow (GB); Subramaniam Ganeshamurugan, London (GB); Muttulingam Kumaraverl, Ealing (GB); Arumugam Partheepan, Ilford (GB); Gnanamoly Paramaswara, London (GB); Juan Antipan-Lara, London (GB)

(73) Assignee: Merck Patent GmbH, Darmstadt (DE)

( * ) Notice: Subject to any disclaimer, the term of this patent is extended or adjusted under 35 U.S.C. 154(b) by 1134 days.

(21) Appl. No.: 11/629,566

(22) PCT Filed: Jun. 30, 2005

(86) PCT No.: PCT/GB2005/002584
§ 371 (c)(1),
(2), (4) Date: Dec. 14, 2006

(87) PCT Pub. No.: WO2006/003408
PCT Pub. Date: Jan. 12, 2006

(65) Prior Publication Data
US 2007/0235728 A1    Oct. 11, 2007

(30) Foreign Application Priority Data

Jun. 30, 2004  (GB) .................................. 0414640.3
Jul. 8, 2004   (GB) .................................. 0415315.1

(51) Int. Cl.
*H01L 51/54*  (2006.01)
*C09K 11/06*  (2006.01)

(52) U.S. Cl. ........ 428/690; 428/917; 313/504; 313/506; 257/E51.044; 252/301.16; 546/2; 546/4; 548/101; 548/108; 549/3

(58) Field of Classification Search ........................ None
See application file for complete search history.

(56) References Cited

U.S. PATENT DOCUMENTS

| | | | |
|---|---|---|---|
| 2002/0034656 A1* | 3/2002 | Thompson et al. | 428/690 |
| 2002/0134984 A1* | 9/2002 | Igarashi | 257/79 |
| 2002/0182441 A1* | 12/2002 | Lamansky et al. | 428/690 |
| 2004/0065544 A1 | 4/2004 | Igarashi et al. | |

FOREIGN PATENT DOCUMENTS

| | | |
|---|---|---|
| EP | 1 238 981 | 9/2002 |
| EP | 1 239 526 | 9/2002 |
| WO | WO 03/091355 | 11/2003 |
| WO | WO 2004/020504 | 3/2004 |
| WO | WO 2004/101707 | 11/2004 |

OTHER PUBLICATIONS

CIE Color Space graph, retrieved on May 25, 2010 from <http://teachpsych.org/resources/e-books/faces/script/Ch09_HTM/E-figs_files/cie1931.jpg>.

B. Jankovic & S. Mentus, Model-Fitting & Model-Free Analysis of Thermal Decomposition of Palladium Acetylacetonate, J. Thermal Analysis&Calorimetry, vol. 94(2008) 2, 395-403.

Tsuboyama et al., Homoleptic Cyclometalated Iridium Complexes w/ Highly Efficient Red Phosphorescence & Appl. to Org. Light-Emitting Diode, J.Am.Chem.Soc. 2003, 125, 12971-79.

* cited by examiner

*Primary Examiner* — Marie R. Yamnitzky
(74) *Attorney, Agent, or Firm* — David Silverstein; Andover-IP-Law

(57) ABSTRACT

Electroluminescent devices have an electroluminescent layer incorporating iridium complexes with 2-benzo[b]thiophenyl and benzimidazole ligands such as bis[thiophen-2-yl-pyridine-$C^2$,N']-2-(2-pyridyl)-benzimidazole iridium.

32 Claims, 21 Drawing Sheets

Alq

Bebq

BAlq1

ZnPBO

ZnPBT

DTVbi or

HTM-1

TPTE

ITO (100 nm)/CuPc (10 nm)/α-NPB (60 nm)/CBP : Compound X (30 : 2 nm)/BCP (6 nm)/Zrq$_4$ (30 nm)/LiF (0.5 nm)/Al ITO (100 nm)/CuPc (10 nm)/α-NPB (60 nm)/CBP : Compound X (30 : 2 nm)/BCP (6 nm)/Zrq₄ (30 nm)/LiF (0.5 nm)/Al ITO (100 nm)/CuPc (10 nm)/α-NPB (60 nm)/Liq : Compound X (30 : 2 nm)/BCP (6 nm)/Zrq$_4$ (30 nm)/LiF (0.5 nm)/Al ITO (100 nm)/CuPc (10 nm)/α-NPB (60 nm)/Al(dbm)$_3$ : Compound X (30 : 2 nm)/BCP (6 nm)/Zrq$_4$ (30 nm)/LiF (0.5 nm)/Al

CBP

BAlq$_2$

Complex A

Complex B

Zrq$_4$ (1)ITO (110 nm)/(2)Complex A(10 nm)/(3)α-NPB (60 nm)/(4)CBP : Compound X (30 : 2 nm)/(5) Zrq$_4$(30 nm)/LiF (0.5 nm)/Al (1)ITO (110 nm)/(2)Complex A(10 nm)/(3)α-NPB (60 nm)/(4)CBP : Compound X (30 : 2 nm)/(5) Zrq$_4$(30 nm)/LiF (0.5 nm)/Al (1)ITO (110 nm)/(2)Complex A (10 nm)/(3)α-NPB (60 nm)/(4)BAlq$_2$ : Compound X (30 : 2 nm)/(5) Zrq$_4$(30 nm)/LiF (0.5 nm)/Al (1)ITO (110 nm)/(2)Complex A (10 nm)/(3)α-NPB (60 nm)/(4)BAlq₂ : Compound X (30 : 2 nm)/(5) Zrq₄(30 nm)/LiF (0.5 nm)/Al (1)ITO (110 nm)/(2)Complex A (10 nm)/(3)α-NPB (60 nm)/(4)Complex B : Compound X (30 : 2 nm)/(5) Zrq$_4$(30 nm)/LiF (0.5 nm)/Al

ELECTROLUMINESCENT MATERIALS AND DEVICES

CROSS-REFERENCE TO RELATED APPLICATIONS

This application is a national stage application of international application PCT/GB05/02584, filed Jun. 30, 2005, which claims the benefit of the filing dates of United Kingdom application nos. 0414640.3 filed Jun. 30, 2004, and 0415315.1, filed Jul. 8, 2004.

The present invention relates to electroluminescent materials and to electroluminescent devices.

Materials that emit light when an electric current is passed through them are well known and used in a wide range of display applications. Devices which are based on inorganic semiconductor systems are widely used. However these suffer from the disadvantages of high energy consumption, high cost of manufacture, low quantum efficiency and the inability to make flat panel displays. Organic polymers have been proposed as useful in electroluminescent devices, but it is not possible to obtain pure colours; they are expensive to make and have a relatively low efficiency. Another electroluminescent compound which has been proposed is aluminium quinolate, but it requires dopants to be used to obtain a range of colours and has a relatively low efficiency.

Patent application WO98/58037 describes a range of transition metal and lanthanide complexes which can be used in electroluminescent devices which have improved properties and give better results. Patent Applications PCT/GB98/01773, PCT/GB99/03619, PCT/GB99/04030, PCT/GB99/04024, PCT/GB99/04028 and PCT/GB00/00268 describe electroluminescent complexes, structures and devices using rare earth chelates. U.S. Pat. No. 5,128,587 discloses an electroluminescent device which consists of an organometallic complex of rare earth elements of the lanthanide series sandwiched between a transparent electrode of high work function and a second electrode of low work function, with a hole conducting layer interposed between the electroluminescent layer and the transparent high work function electrode, and an electron conducting layer interposed between the electroluminescent layer and the electron injecting low work function anode. The hole conducting layer and the electron conducting layer are required to improve the working and the efficiency of the device. The hole transporting layer serves to transport holes and to block the electrons, thus preventing electrons from moving into the electrode without recombining with holes. The recombination of carriers therefore mainly takes place in the emitter layer.

DETAILED DESCRIPTION OF THE INVENTION

Figure 1:
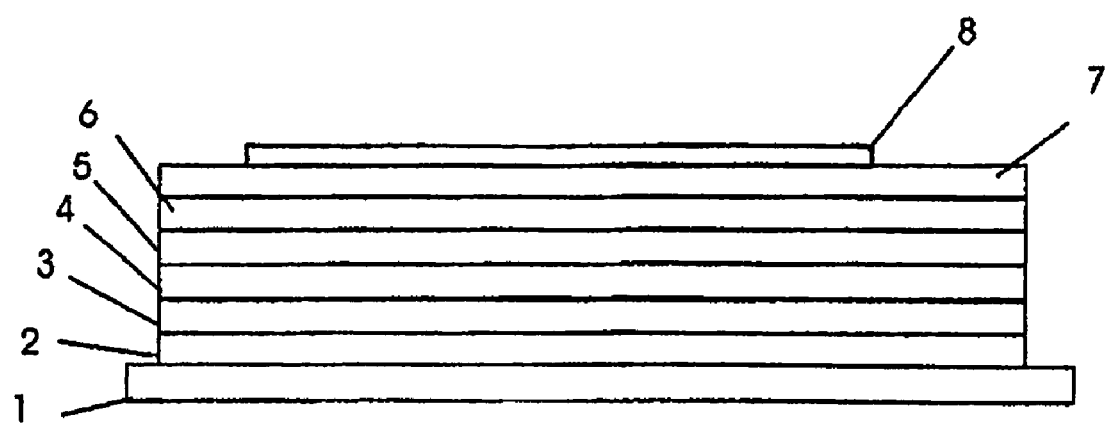
FIG. 1 is a representative electroluminescent device structure fabricated in accordance with this invention as described in Examples 2 to 7.

We have now discovered fiuther electroluminescent organometallic complexes.

According to the invention there is provided complexes of formula:

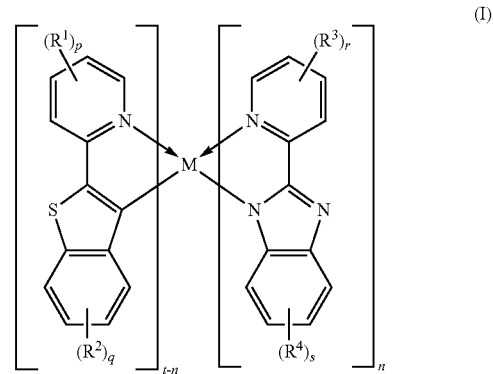

(I)

wherein
M is ruthenium, rhodium, or iridium;
t is 3 and n is 1 or 2;
M is palladium or platinum;
t is 2 and n is 1;
M is osmium;
t is 3 and n is 1 or 2; or
t is 4 and n is 1, 2 or 3;
$R^1$, $R^2$, $R^3$ and $R^4$ can be the same or different and are selected from
  substituted and unsubstituted hydrocarbyl groups
  substituted and unsubstituted monocyclic and polycyclic heterocyclic groups;
  substituted and unsubstituted hydrocarbyloxy or carboxy groups;
  fluorocarbyl groups;
  halogen;
  nitrile;
  amino;
  alkylamino;
  dialkylamino;
  arylamino;
  diarylamino; and
  thiophenyl;

p, q, r and s independently are 0, 1, 2 or 3;
subject to the proviso that where any of p, q, r and s is 2 or 3 only one of them can be other than saturated hydrocarbyl or halogen.

Preferred compounds of the above class are those in which M is iridium. The preferred value for n is 1.

According to the invention there is provided in an alternative formulation complexes of formula:

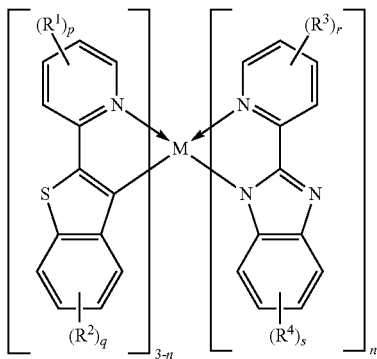

wherein
M is ruthenium, rhodium, palladium, osmium, iridium or platinum;
n is 1 or 2;
$R^1$, $R^2$, $R^3$ and $R^4$ can be the same or different and are selected from
  substituted and unsubstituted hydrocarbyl groups
  substituted and unsubstituted monocyclic and polycyclic heterocyclic groups;
  substituted and unsubstituted hydrocarbyloxy or carboxy groups;
  fluorocarbyl groups;
  halogen;
  nitrile;
  amino;
  alkylamino;
  dialkylamino;
  arylamino;
  diarylamino; and
  thiophenyl;
p, q, r and s independently are 0, 1, 2 or 3;
subject to the proviso that where any of p, q, r and s is 2 or 3 only one of them can be other than saturated hydrocarbyl or halogen.

Preferred compounds of the above class are those in which M is iridium. The preferred value for n is 1.

In those compounds which are ring-substituted, $R^1$, $R^2$, $R^3$ and $R^4$ may be substituted or unsubstituted aliphatic or cycloaliphatic group which may typically be $C_1$-$C_{12}$ and in the case of a cycloaliphatic group are preferably based on cyclopentyl or cyclohexyl. Where $R^1$, $R^2$, $R^3$ and $R^4$ are alkyl they are preferably $C_1$-$C_4$ especially methyl or ethyl. $R^1$, $R^2$, $R^3$ and $R^4$ may also be alkyl or alkoxy in which the alkyl group is preferably $C_1$-$C_{12}$, more preferably $C_1$-$C_4$. Thus preferred values for at least one of $R^1$, $R^2$, $R^3$ and $R^4$ are methyl, ethyl, n-propyl, i-propyl. s-butyl, t-butyl, cyclohexyl, methoxy or ethoxy. In further possibilities, at least one of $R^1$, $R^2$, $R^3$ and $R^4$ is a substituted or unsubstituted monocyclic or polycyclic aromatic, aryloxy or heterocyclic structure. For example, at least one of $R^1$, $R^2$, $R^3$ and $R^4$ may be phenyl, tolyl, fluorophenyl, biphenyl, naphthyl, fluorenyl, anthracenyl, phenanthrenyl or carbazolyl. Other possibilities for at least one of $R^1$, $R^2$, $R^3$ and $R^4$ are fluoro, chloro, methylamino, dimethylamino, benzylamino or dibenzylamino.

A particular compound of formula (I) above is that in which M is Ir, n is 1 and p, q, r and s are 0.

According to a further aspect of the invention, there is also provided a process for manufacturing a compound of formula (I) as defined above.

Synthesis of one of the ligands may be achieved by a Suzuki coupling of a 2-bromopyridine with a benzo[b]thiophene-2-boronic acid or substituted derivative thereof (arylboronic acids are readily prepared from aryllithiums or Grignard reagents and trialkyl borates) using a palladium (0) catalyst, for example tetrakis(triphenylphosphine) palladium e.g. according to the scheme shown below:

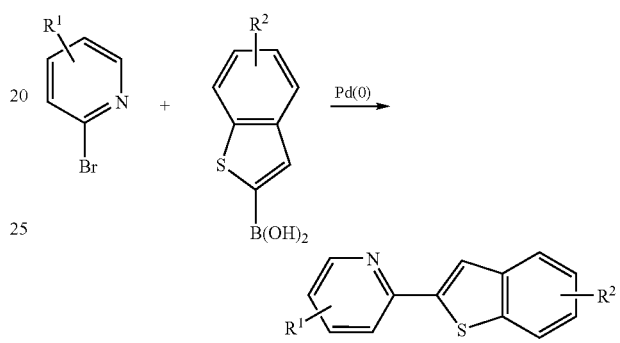

Heating benzo[b]thiophen-2-yl-pyridine or a substituted derivative thereof with iridium trichloride gives e.g. the following complex:

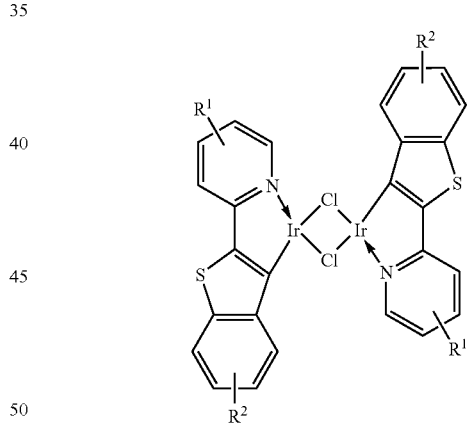

Further treatment of the above complex with a strong base and addition of (2-pyridyl)benzimidazole or a substituted derivative thereof produces the compound of formula (I), the substituents having the same meanings as for formula (I).

In the first step, instead of benzo[b]thiophene there may be used, for example, 4-methylbenzothiophene, 5-methylbenzothiophene, 6-methylbenzothiophene, 7-methylbenzothiophene, 5,7-dimethylbenzothiophene, 5-chlorobenzothiophene or 5-nitrobenzothiophene. Instead of 2-bromopyridine there may be used, for example, 2-chloro-5-iodopyridine, 2-bromo-5-iodopyridine or 2-amino-5-iodopyridine.

The invention also provides an electroluminescent device which comprises (i) a first electrode, (ii) a layer of an electroluminescent material of formula (I) above and (iii) a second electrode.

The thickness of the layer of the electroluminescent material is preferably from 10-250 nm, more preferably 20-75 nm.

The first electrode can function as the anode and the second electrode can function as the cathode and preferably there is a layer of a hole transporting material between the anode and the layer of the electroluminescent compound.

The hole transporting material can be any of the hole transporting materials used in electroluminescent devices.

The hole transporting material can be an amine complex such as α-NBP, poly (vinylcarbazole), N,N'-diphenyl-N,N'-bis(3-methylphenyl)-1,1'-biphenyl-4,4'-diamine (TPD), an unsubstituted or substituted polymer of an amino substituted aromatic compound, a polyaniline, substituted polyanilines, polythiophenes, substituted polythiophenes, unsubstituted and substituted polysilanes etc. Examples of polyanilines are polymers of:

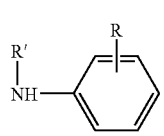

(II)

where R is in the ortho- or meta-position and is hydrogen, C1-18 alkyl, C1-6 alkoxy, amino, chloro, bromo, hydroxy or the group:

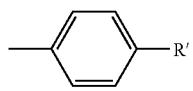

where R is alkyl or aryl and R' is hydrogen, C1-6 alkyl or aryl with at least one other monomer of formula II above.

Alternatively the hole transporting material can be a polyaniline. Polyanilines which can be used in the present invention have the general formula:

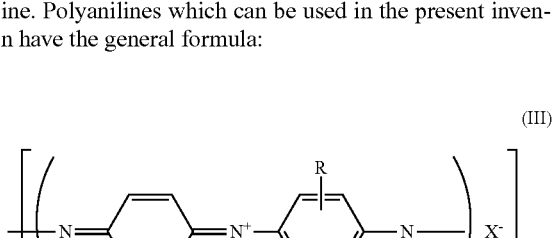

(III)

where p is from 1 to 10 and n is from 1 to 20, R is as defined above and X is an anion, preferably selected from Cl, Br, $SO_4$, $BF_4$, $PF_6$, $H_2PO_3$, $H_2PO_4$, arylsulphonate, arenedicarboxylate, polystyrenesulphonate, polyacrylate alkylsulphonate, vinylsulphonate, vinylbenzene sulphonate, cellulose sulphonate, camphor sulphonate, cellulose sulphate or a perfluorinated polyanion.

Examples of arylsulphonates are p-toluenesulphonate, benzenesulphonate, 9,10-anthraquinone-sulphonate and anthracenesulphonate. An example of an arenedicarboxylate is phthalate and an example of arenecarboxylate is benzoate.

We have found that protonated polymers of the unsubstituted or substituted polymer of an amino substituted aromatic compound such as a polyaniline are difficult to evaporate or cannot be evaporated. However we have surprisingly found that if the unsubstituted or substituted polymer of an amino substituted aromatic compound is deprotonated, then it can be easily evaporated, i.e. the polymer is evaporable.

Preferably evaporable deprotonated polymers of unsubstituted or substituted polymers of an amino substituted aromatic compound are used. The deprotonated unsubstituted or substituted polymer of an amino substituted aromatic compound can be formed by deprotonating the polymer by treatment with an alkali such as ammonium hydroxide or an alkali metal hydroxide such as sodium hydroxide or potassium hydroxide.

The degree of protonation can be controlled by forming a protonated polyaniline and deprotonating. Methods of preparing polyanilines are described in the article by A. G. MacDiarmid and A. F. Epstein, Faraday Discussions, Chem Soc. 88 P319, 1989.

The conductivity of the polyaniline is dependent on the degree of protonation with the maximum conductivity being when the degree of protonation is between 40 and 60%, for example about 50%.

Preferably the polymer is substantially fully deprotonated.

A polyaniline can be formed of octamer units. i.e. p is four, e.g.

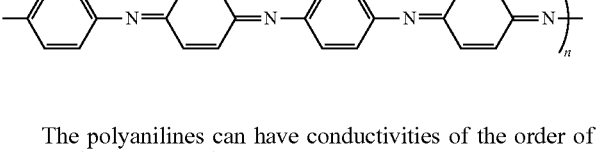

The polyanilines can have conductivities of the order of $1 \times 10^{-1}$ Siemen $cm^{-1}$ or higher.

The aromatic rings can be unsubstituted or substituted, e.g. by a C1 to 20 alkyl group such as ethyl.

The polyaniline can be a copolymer of aniline and preferred copolymers are the copolymers of aniline with o-anisidine, m-sulphanilic acid or o-aminophenol, or o-toluidine with o-aminophenol, o-ethylaniline, o-phenylene diamine or with amino anthracenes.

Other polymers of an amino substituted aromatic compound which can be used include substituted or unsubstituted polyaminonapthalenes, polyaminoanthracenes, polyaminophenanthrenes, etc. and polymers of any other condensed polyaromatic compound. Polyaminoanthracenes and methods of making them are disclosed in U.S. Pat. No. 6,153,726. The aromatic rings can be unsubstituted or substituted, e.g. by a group R as defined above.

Other hole transporting materials are conjugated polymers and the conjugated polymers which can be used can be any of the conjugated polymers disclosed or referred to in U.S. Pat. No. 5,807,627, WO90/13148 and WO92/03490.

The preferred conjugated polymers are poly (p-phenylenevinylene) (PPV) and copolymers including PPV. Other preferred polymers are poly(2,5 dialkoxyphenylene vinylene) such as poly[2-methoxy-5-(2-methoxypentyloxy-1,4-phenylene vinylene)], poly[(2-methoxypentyloxy)-1,4-phenylenevinylene], poly[(2-methoxy-5-(2-dodecyloxy-1,4-phenylenevinylene)] and other poly(2,5 dialkoxyphenylenevinylenes) with at least one of the alkoxy groups being a long chain solubilising alkoxy group, polyfluorenes and oligofluorenes, polyphenylenes and oligophenylenes, polyanthracenes and oligoanthracenes, polythiophenes and oligothiophenes.

In PPV the phenylene ring may optionally carry one or more substituents, e.g. each independently selected from alkyl, preferably methyl, or alkoxy, preferably methoxy or ethoxy.

In polyfluorene, the fluorene ring may optionally carry one or more substituents e.g. each independently selected from alkyl, preferably methyl, alkoxy, preferably methoxy or ethoxy.

Any poly(arylenevinylene) including substituted derivatives thereof can be used and the phenylene ring in poly(p-phenylenevinylene) may be replaced by a fused ring system such as anthracene or naphthalene ring and the number of vinylene groups in each poly(phenylenevinylene) moiety can be increased, e.g. up to 7 or higher.

The conjugated polymers can be made by the methods disclosed in U.S. Pat. No. 5,807,627, WO90/13148 and WO92/03490.

The thickness of the hole transporting layer is preferably 20 nm to 200 nm.

The polymers of an amino substituted aromatic compound such as polyanilines referred to above can also be used as buffer layers with or in conjunction with other hole transporting materials e.g. between the anode and the hole transporting layer. Other buffer layers can be formed of phthalocyanines such as copper phthalocyanine.

The structural formulae of some other hole transporting materials are shown in FIGS. 4, 5, 6, 7 and 8 of the drawings, where R, $R^1$, $R^2$, $R^3$ and $R^4$ can be the same or different and are selected from hydrogen, substituted and unsubstituted hydrocarbyl groups such as substituted and unsubstituted aliphatic groups, substituted and unsubstituted aromatic, heterocyclic and polycyclic ring structures, fluorocarbon groups such as trifluoromethyl, halogens such as fluorine or thiophenyl groups; R, $R^1$, $R^2$, $R^3$ and $R^4$ can also form substituted and unsubstituted fused aromatic, heterocyclic and polycyclic ring structures and can be copolymerisable with a monomer, e.g. styrene. X is Se, S or O, Y can be hydrogen, substituted or unsubstituted hydrocarbyl groups, such as substituted and unsubstituted aromatic, heterocyclic and polycyclic ring structures, fluorocarbon groups such as trifluoromethyl, halogens such as fluorine, thiophenyl or nitrile groups.

Examples of R and/or $R^1$ and/or $R^2$ and/or $R^3$ and/or $R^4$ include aliphatic, aromatic and heterocyclic groups, alkoxy, aryloxy and carboxy groups, substituted and unsubstituted phenyl, fluorophenyl, biphenyl, naphthyl, fluorenyl, anthracenyl and phenanthrenyl groups, alkyl groups such as t-butyl, and heterocyclic groups such as carbazole.

Figure 2:
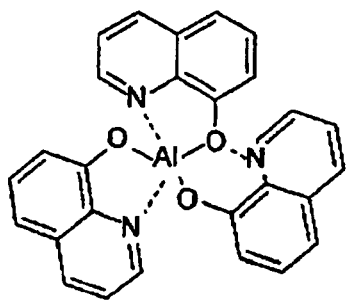
FIGS. 2 and 3 illustrate chemical formulae of certain types of electron injecting materials that may be used in some invention embodiments.
Figure 2:
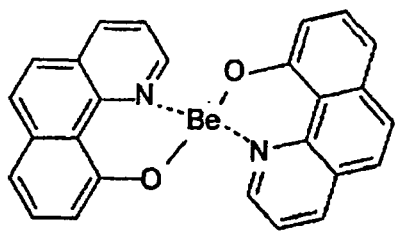
Figure 2:
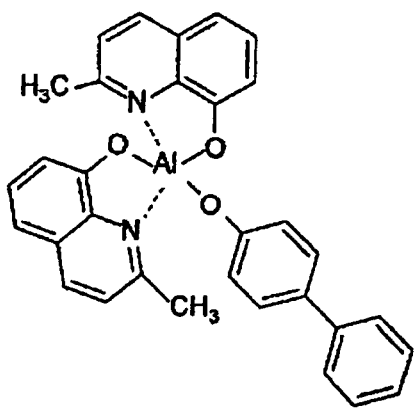
Figure 2:
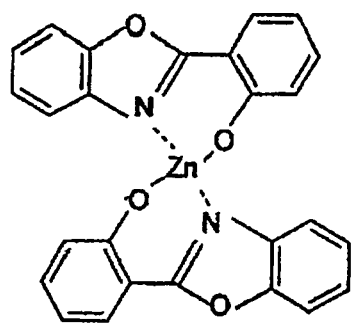
Figure 2:
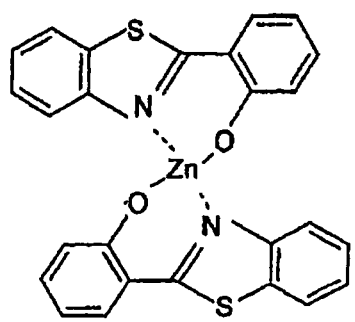
Figure 2:
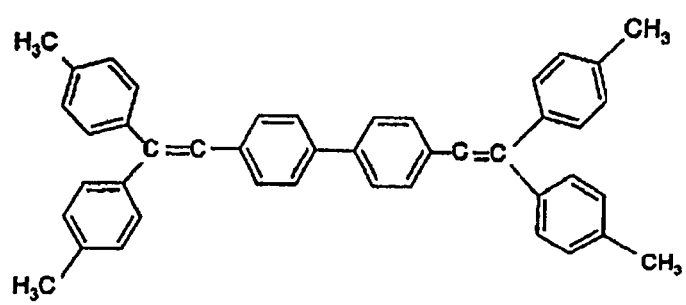
Figure 3:
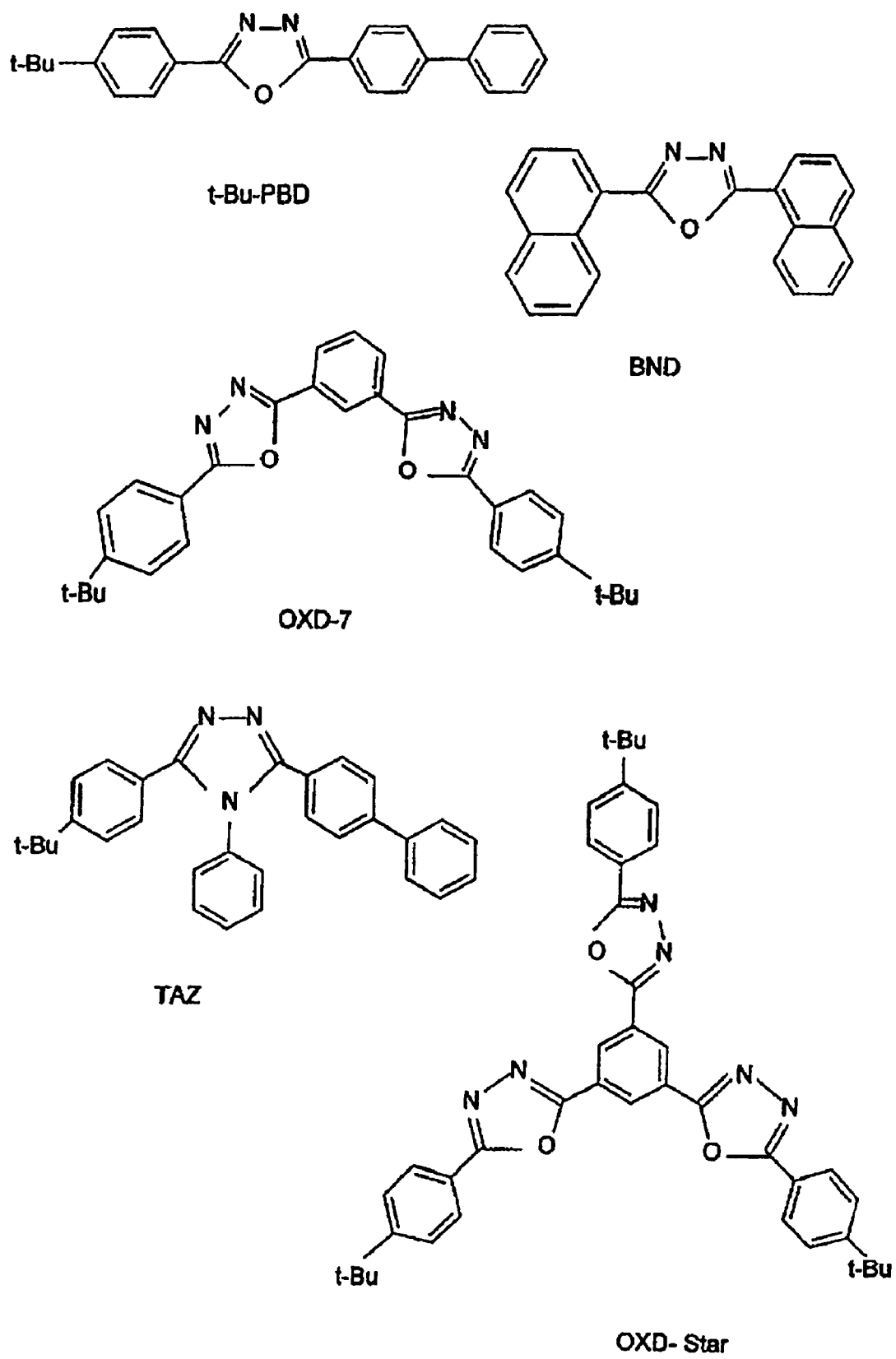
Figure 4:
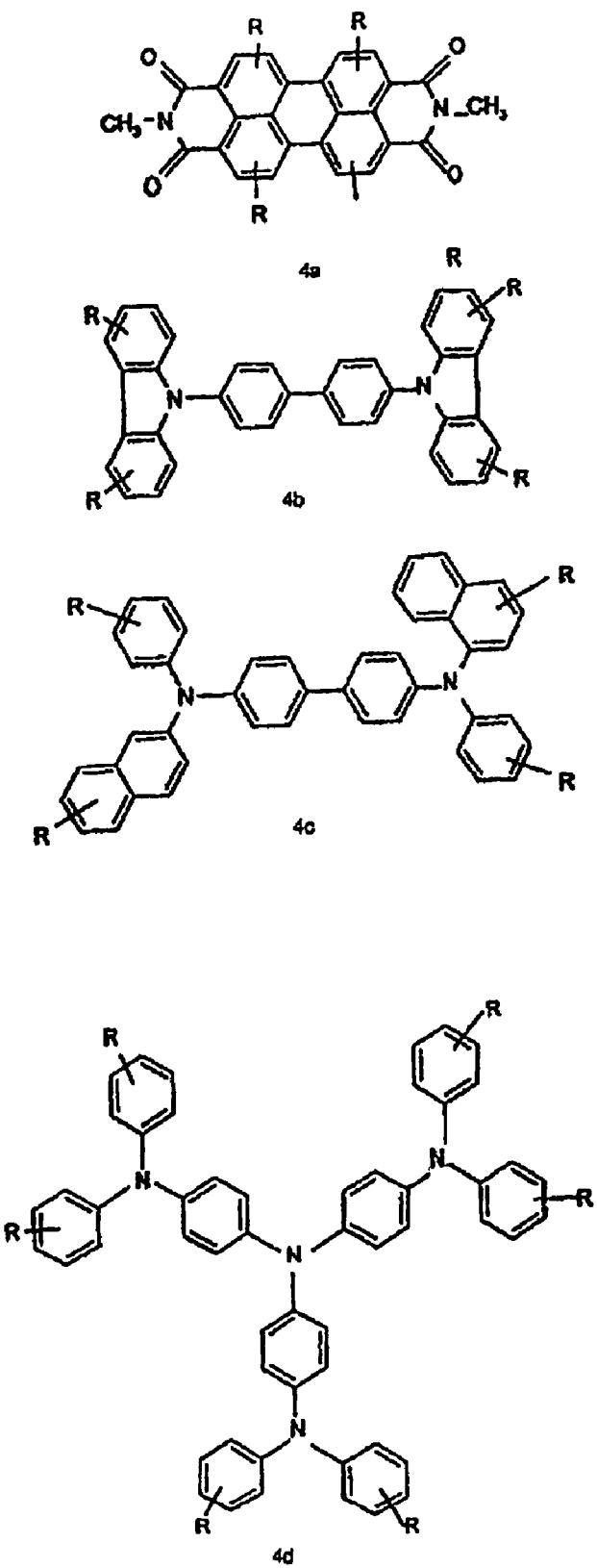
FIGS. 4, 5, 6, 7 and 8 illustrate chemical formulae of certain types of hole transporting materials that may be used in some invention embodiments.
Figure 5:
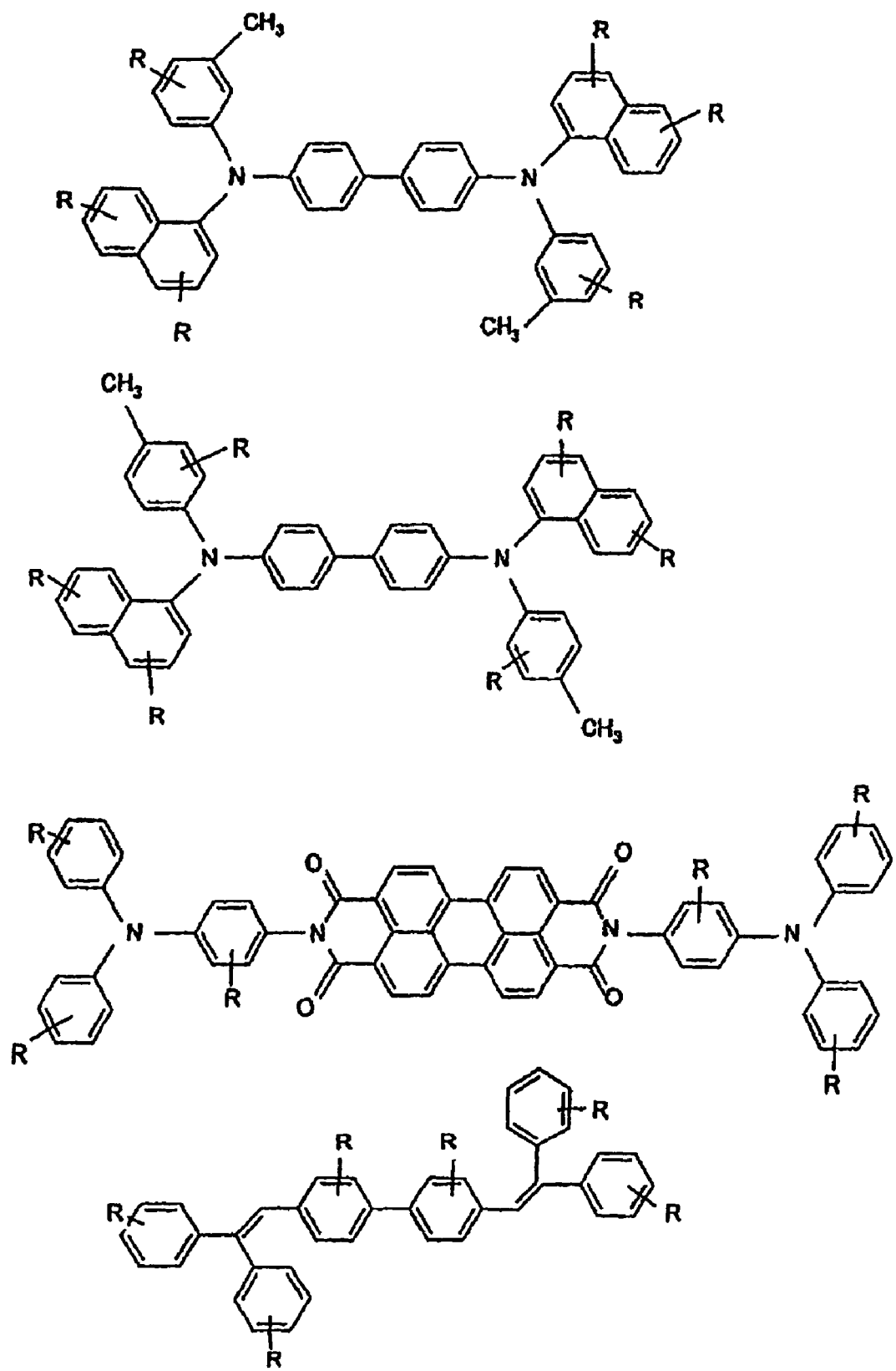
Figure 6:
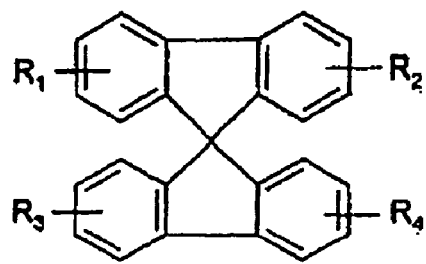
Figure 6:
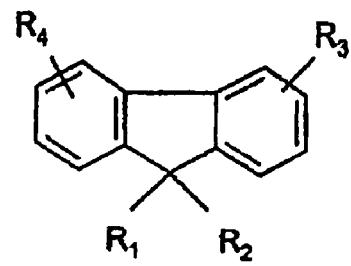
Figure 6:
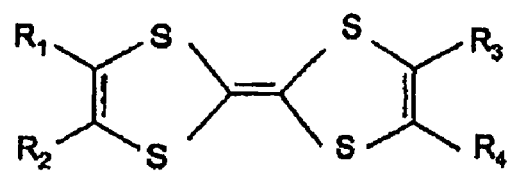
Figure 6:
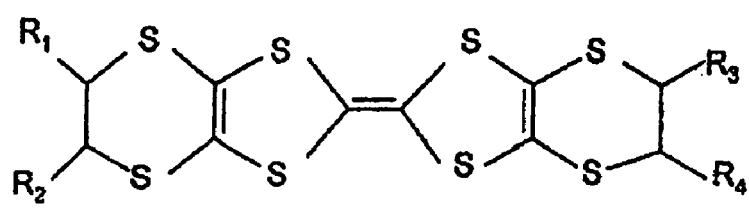
Figure 6:
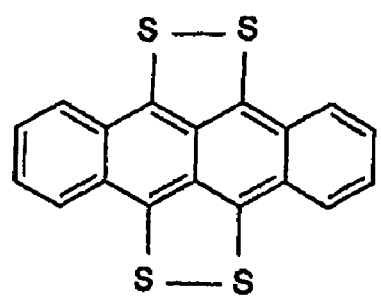
Figure 7:
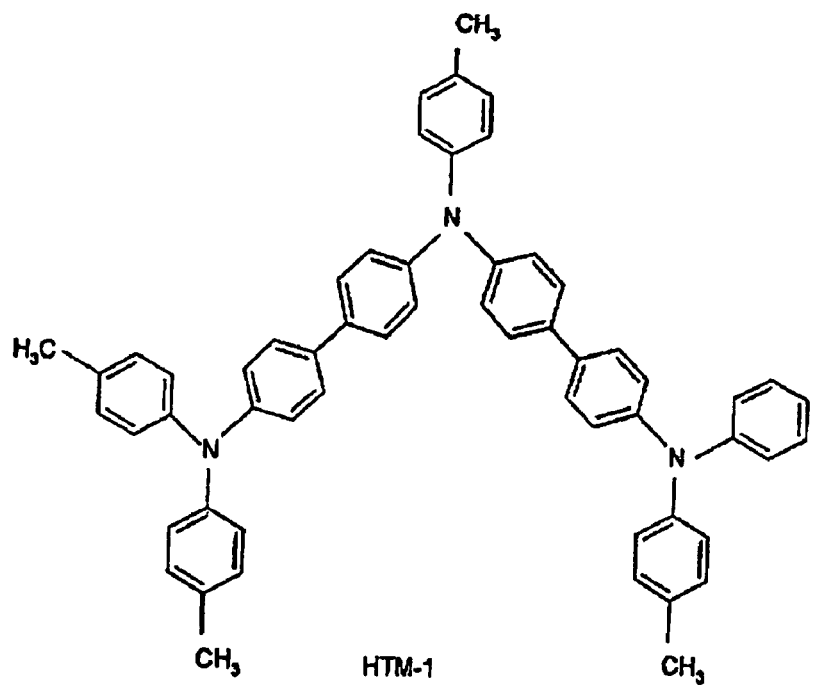
Figure 7:
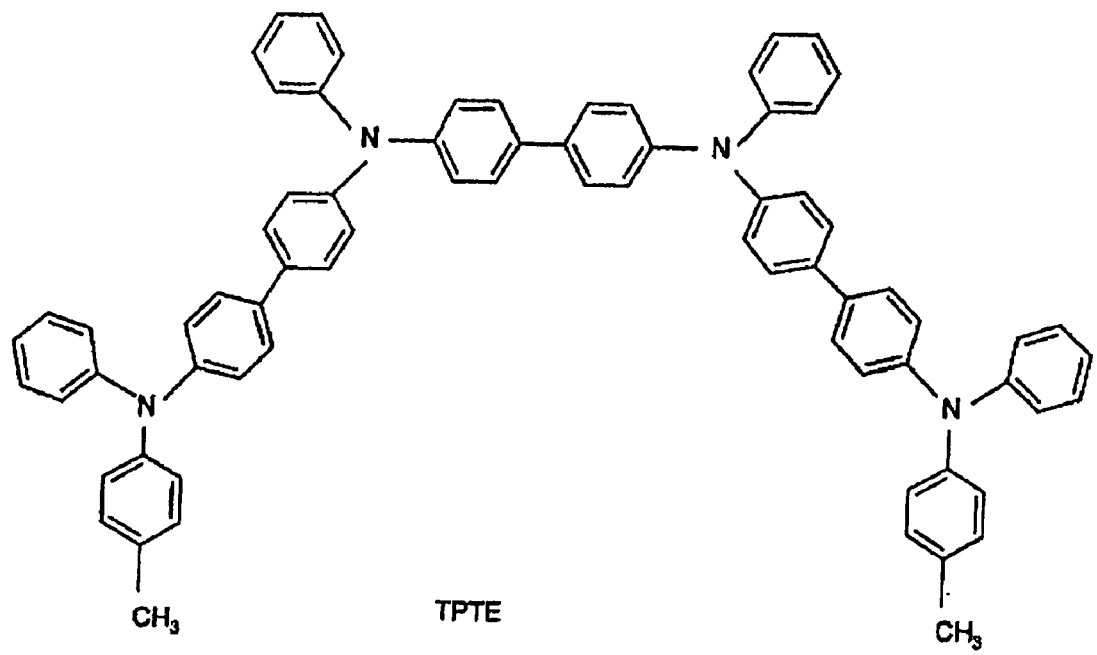
Figure 8:
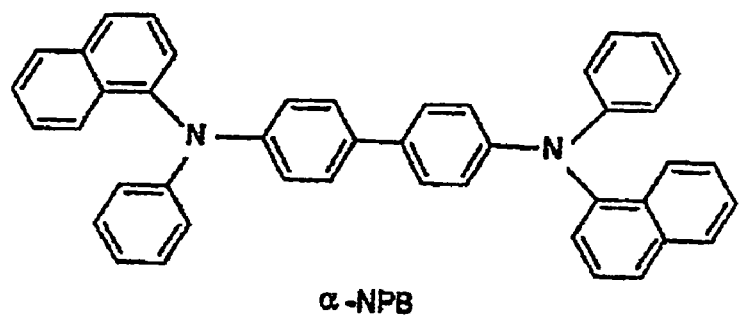
Figure 8:
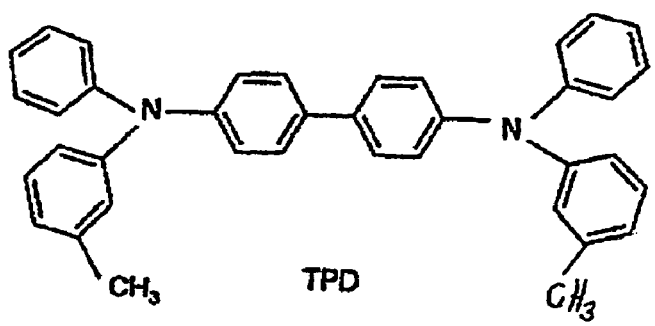
Figure 8:
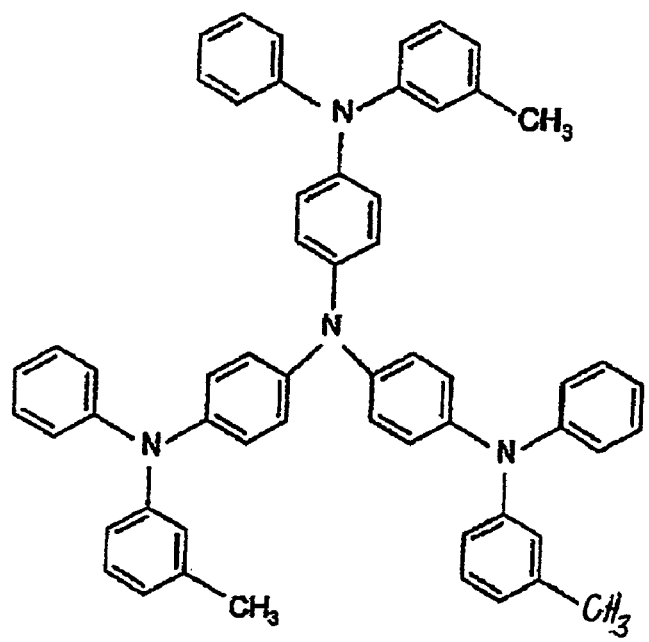

Optionally there is a layer of an electron injecting material between the cathode and the electroluminescent material layer. The electron injecting material is a material which will transport electrons when an electric current is passed through. Electron injecting materials include a metal complex such as a metal quinolate, e.g. an aluminium quinolate, lithium quinolate, zirconium quinolate, a cyanoanthracene such as 9,10-dicyanoanthracene, cyano substituted aromatic compounds, tetracyanoquinodimethane, a polystyrene sulphonate or a compound with the structural formulae shown in FIG. 2 or 3 of the drawings or $Mx(DBM)_n$ where Mx is a metal and DBM is dibenzoyl methane and n is the valency of Mx e.g. Mx is aluminium, chromium or scandium. A Schiff base can also be used in place of the DBM moiety.

Instead of being a separate layer the electron injecting material can be mixed with the electroluminescent material and co-deposited with it.

Optionally the hole transporting material can be mixed with the electroluminescent material and co-deposited with it and the electron injecting materials and the electroluminescent materials can be mixed. The hole transporting materials, the electroluminescent materials and the electron injecting materials can be mixed together to form one layer, which simplifies the construction.

The first electrode is preferably a transparent substrate such as a conductive glass or plastic material which acts as the anode; preferred substrates are conductive glasses such as indium tin oxide coated glass, but any glass which is conductive or has a conductive layer such as a metal or conductive polymer can be used. Conductive polymers and conductive polymer coated glass or plastics materials can also be used as the substrate.

The cathode is preferably a low work function metal, e.g. aluminium, barium, calcium, lithium, rare earth metals, transition metals, magnesium and alloys thereof such as silver/magnesium alloys, rare earth metal alloys etc; aluminium is a preferred metal. A metal fluoride such as an alkali metal e.g. lithium fluoride, potassium fluoride, caesium fluoride or rare earth metal or their alloys can be used as the second electrode, for example by having a metal fluoride layer formed on a metal.

The iridium complex can be mixed with a host material

The devices of the present invention can be used as displays in video displays, mobile telephones, portable computers and any other application where an electronically controlled visual image is used. The devices of the present invention can be used in both active and passive applications of such as displays.

In known electroluminescent devices either one or both electrodes can be formed of silicon and the electroluminescent material and intervening layers of a hole transporting and electron transporting materials can be formed as pixels on the silicon substrate. Preferably each pixel comprises at least one layer of an electroluminescent material and a (at least semi-) transparent electrode in contact with the organic layer on a side thereof remote from the substrate.

Preferably, the substrate is of crystalline silicon, polycrystalline silicon, amorphous silicon or continuously grained silicon and the surface of the substrate may be polished or smoothed to produce a flat surface prior to the deposition of electrode, or electroluminescent compound. Alternatively a non-planarised silicon substrate can be coated with a layer of conducting polymer to provide a smooth, flat surface prior to deposition of further materials.

In one embodiment, each pixel comprises a metal electrode in contact with the substrate. Depending on the relative work functions of the metal and transparent electrodes, either may serve as the anode with the other constituting the cathode.

When the silicon substrate is the cathode an indium tin oxide coated glass or semi-transparent gold can act as the anode and light is emitted through the anode. When the silicon substrate acts as the anode, the cathode can be formed of a transparent electrode which has a suitable work function; for example by an indium zinc oxide coated glass in which the indium zinc oxide has a low work function. The anode can have a transparent coating of a metal formed on it to give a suitable work function. These devices are sometimes referred to as top emitting devices or back emitting devices.

The metal electrode may consist of a plurality of metal layers; for example a higher work function metal such as aluminium deposited on the substrate and a lower work function metal such as calcium deposited on the higher work function metal. In another example, a further layer of conducting polymer lies on top of a stable metal such as aluminium.

Preferably, the electrode also acts as a mirror behind each pixel and is either deposited on, or sunk into, the planarised surface of the substrate. However, there may alternatively be a light absorbing black layer adjacent to the substrate.

In still another embodiment, selective regions of a bottom conducting polymer layer are made non-conducting by exposure to a suitable aqueous solution allowing formation of arrays of conducting pixel pads which serve as the bottom contacts of the pixel electrodes.

The invention is illustrated in the following Examples.

EXAMPLE 1

2-Benzo[b]thiophen-2-yl-pyridine

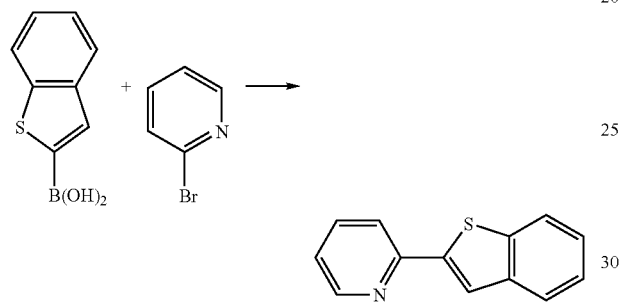

A two-necked 250 mL round-bottomed flask fitted with a reflux condenser (with gas inlet) and a rubber septum was flushed with argon before 2-bromopyridine (2.57 mL, 27 mmol) and ethyleneglycol dimethylether (80 mL, dry and degassed) were introduced. Tetrakis(triphenylphosphine)palladium (1.0 g, 0.87 mmol) was added and the solution stirred at room temperature for 10 minutes. Benzothiophene-2-boronic acid (5.0 g, 28.1 mmol) was then added, followed by anhydrous sodium bicarbonate (8.4 g, 100 mmol) and water (50 mL, degassed). The septum was replaced with a glass stopper and the reaction mixture was heated at 80° C. for 16 hours, cooled to room temperature and the volatiles removed in vacuo. Organics were extracted with ethyl acetate (3×100 mL), washed with brine and dried over magnesium sulfate. Removal of the organics yielded a pale yellow solid. Recrystallisation from ethanol yielded a colourless solid (3.9 g, 68%, two crops), m.p. 124-6° C.

Tetrakis[2-benzo][b]thiophen-2-yl-pyridine-$C^2$,N']($\mu$-chloro)diiridium

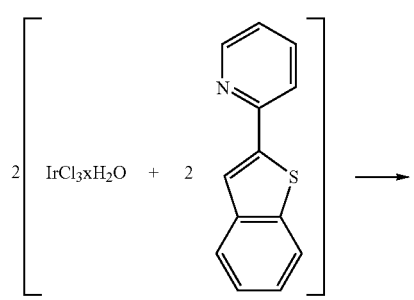

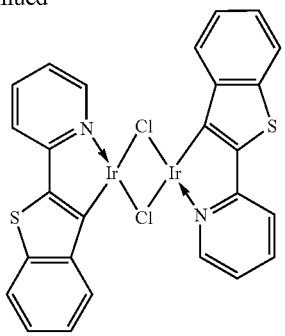

Iridium trichloride hydrate (0.97 g, 3.24 mmol) was combined with 2-benzo[b]thiophen-2-yl-pyridine (2.05 g, 9.7 mmol), dissolved in a mixture of 2-ethoxyethanol (70 mL, dried and distilled over MgSO$_4$, degassed) and water (20 mL, degassed), and refluxed for 24 hours. The solution was cooled to room temperature and the orange precipitate collected on a glass sinter. The precipitate was washed with ethanol (60 mL, 95%), acetone (60 mL), and hexane. This was dried and used without further purification. Yield (1.5 g. 71%)

Bis[thiophen-2-yl-pyridine-$C^2$,N']-2-(2-pyridyl)benzimidazole iridium

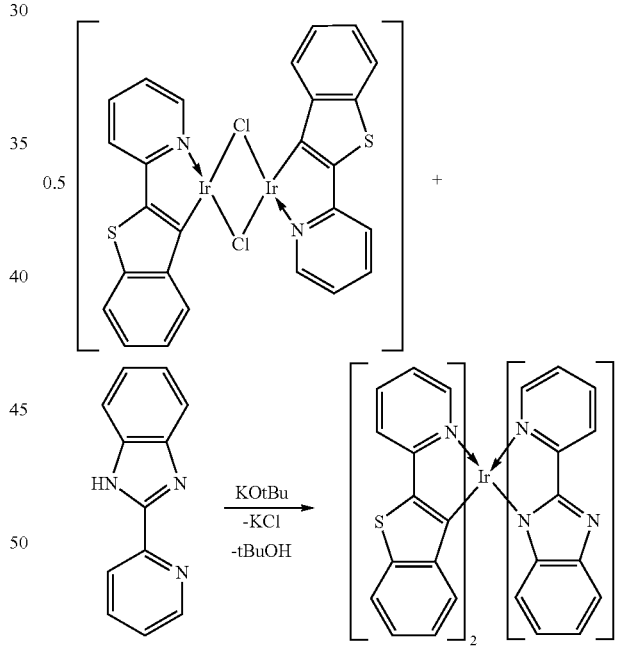

Potassium tert-butoxide (1.12 g, 10 mmol) and 2-(2-pyridyl)benzimidazole (1.95 g, 10 mmol) were added to a 200 mL Schlenk tube under an inert atmosphere. 2-Ethoxyethanol (dried and distilled over magnesium sulfate, 100 mL) was added and the resultant solution stirred at ambient temperature for 10 minutes. Tetrakis[2-benzo[b]thiophen-2-yl-pyridine-$C^2$,N']($\mu$-chloro)diiridium (6.0 g, 4.62 mmol) was added and the mixture refluxed under an inert atmosphere for 16 hours. On cooling to room temperature, an orange/red solid separated out. The solid was collected by filtration and washed with ethanol (3×100 mL) and diethyl ether (100 mL). After drying in vacuo the material was purified by soxhlet extraction with ethyl acetate for 24 hours. Further purification was achieved by high-vacuum sublimation ($3\times10^{-7}$ Torr, 400° C.). Yield (6.6 g, 89%, pre-sublimation).

Elemental Analysis:
Calc.: C, 56.56; H, 3.00, N, 8.68
Found: C, 56.41; H, 2.91; N, 8.64

EXAMPLE 2

Device 1

A pre-etched ITO (indium tin oxide) coated glass piece ($10\times10$ cm$^2$) was used. The device was fabricated by sequentially forming on the ITO, by vacuum evaporation using a Solciet Machine (ULVAC Ltd, Chigacki, Japan); the active area of each pixel was 3 mm by 3 mm, the layers comprised:
(1) ITO (100 nm)/(2) CuPc (10 nm)/(3) α-NPB (60 nm)/(4) Liq:Compound X (30:2 nm)/(5) BCP(6 nm)/(6) Zrq$_4$ (30 nm)/(7) LiF (0.5 nm)/Al The device structure is shown in FIG. 1. Where Compound X is Bis[thiophen-2-yl-pyridine-C$^2$,N']-2-(2-pyridyl)-benzimidazole iridium synthesised as above, CuPc is a copper phthalocyanine buffer layer, α-NPB is as in FIG. 8, Liq is lithium quinolate, BCP is bathocupron, Zrq$_4$ is as in FIG. 15 and LiF is lithium fluoride.

The ITO electrode was always connected to the positive terminal. The current vs. voltage studies were carried out on a computer controlled Keithly 2400 source meter.

Figure 11:
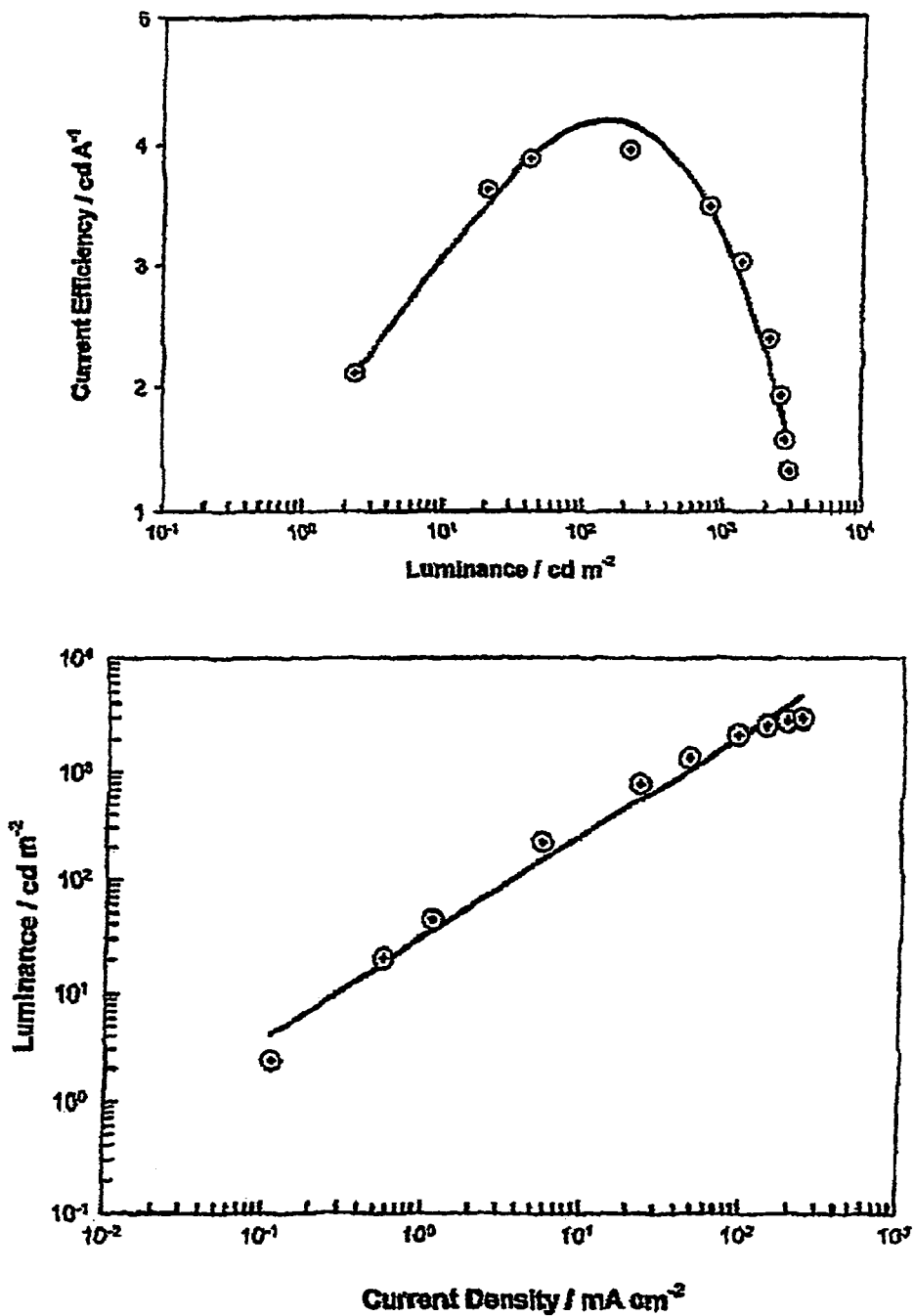
FIGS. 11 and 12 illustrate the electroluminescent properties of an electroluminescent device according to the present invention fabricated in accordance with Example 2.
Figure 12:
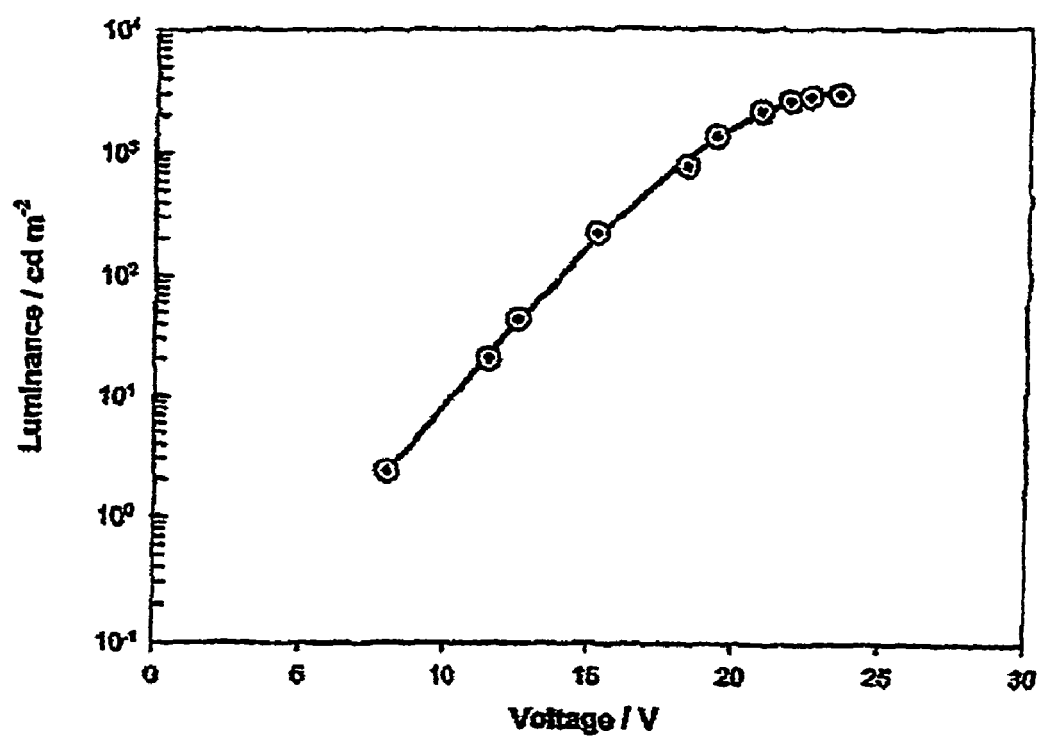

The electroluminescent properties were measured and the results are shown in FIGS. 11 and 12. The electroluminescent device on which FIGS. 11 and 12 are based demonstrated CIE coordinates of x=0.64 and y=0.35 and produced a peak luminescent wave length of about 600 nm.

EXAMPLE 3

Device 2

Figure 9:
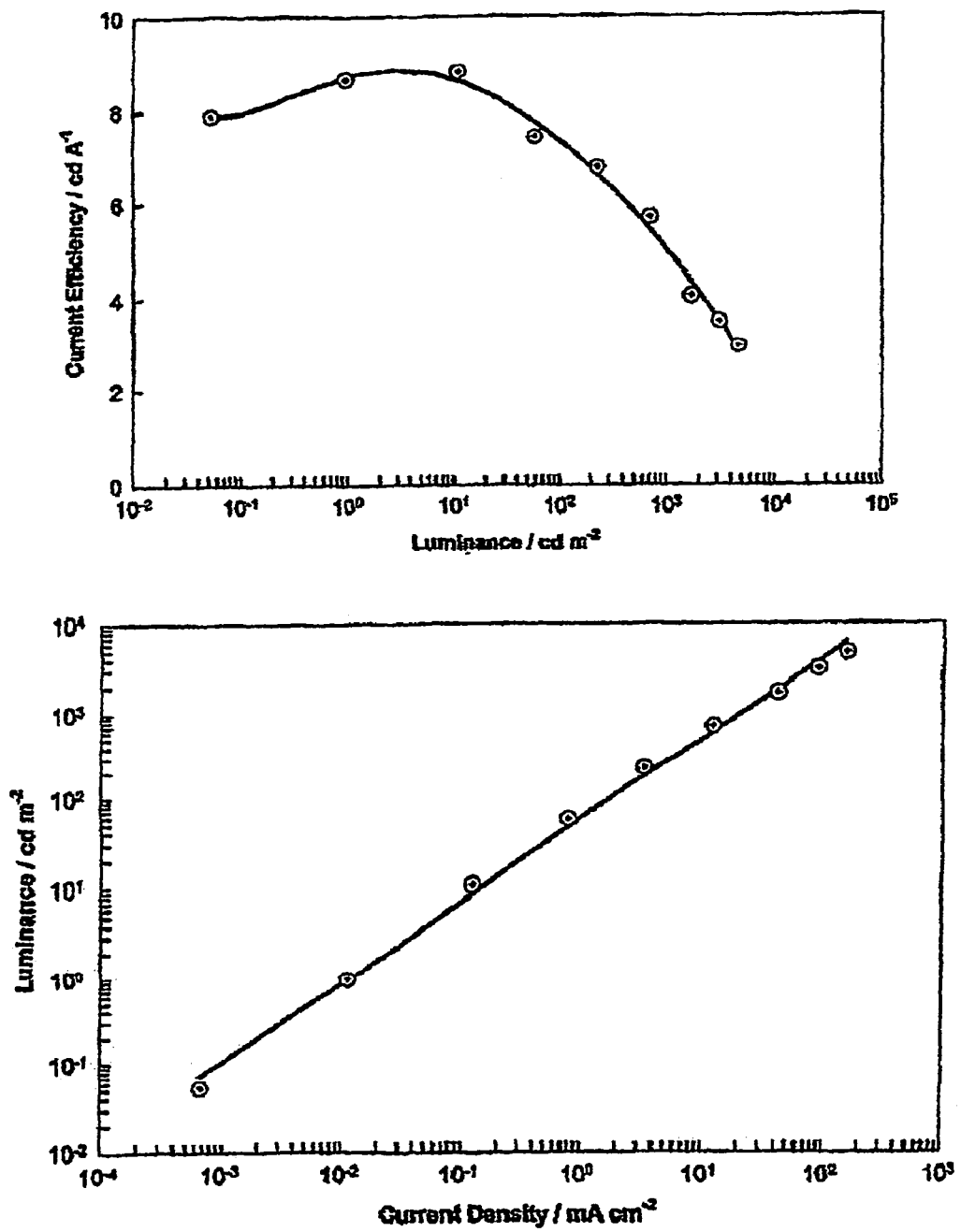
FIGS. 9 and 10 illustrate the electroluminescent properties of an electroluminescent device according to the present invention fabricated in accordance with Example 3.
Figure 10:
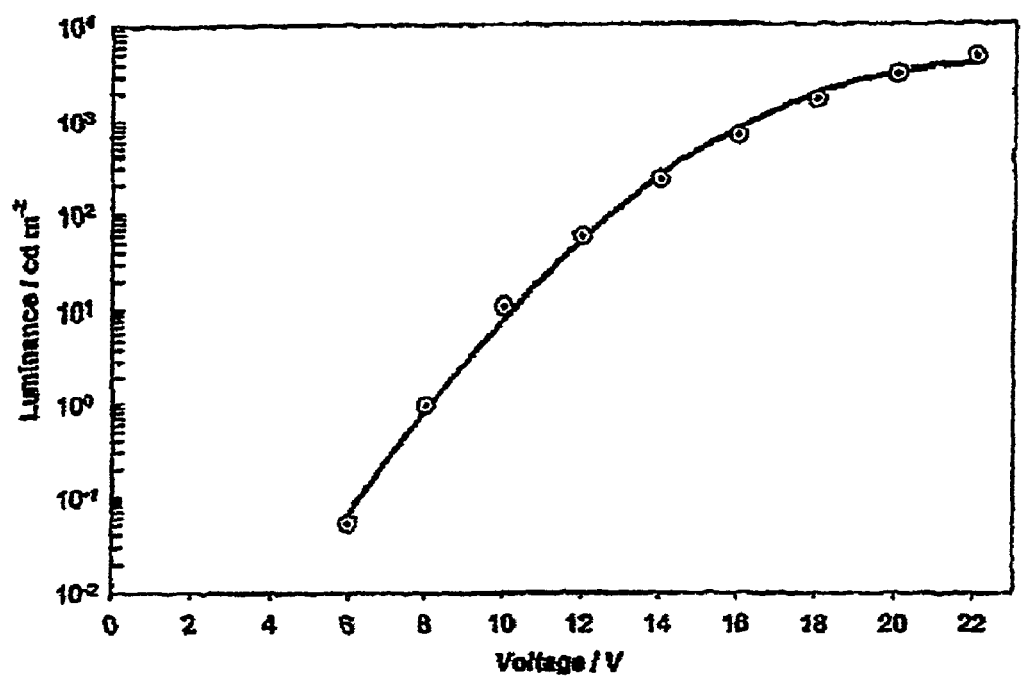

A device was made as in Example 2 except that it had the structure:
(1) ITO (100 nm)/(2) CuPc (10 nm)/(3) α-NPB (60 nm)/(4) CBP:Compound X (30:2 nm)/(5)BCP (6 nm)/(6) Zrq$_4$ (30 nm)/(7) LiF (0.5 nm)/Al Where CBP is as in FIG. 15. The electroluminescent properties were measured and the results are shown in FIGS. 9 and 10. The electroluminescent device on which FIGS. 9 and 10 are based demonstrated CIE coordinates of x=0.639 and y=0.356 and produced a peak luminescent wave length of about 600 nm.

EXAMPLE 4

Device 3

Figure 13:
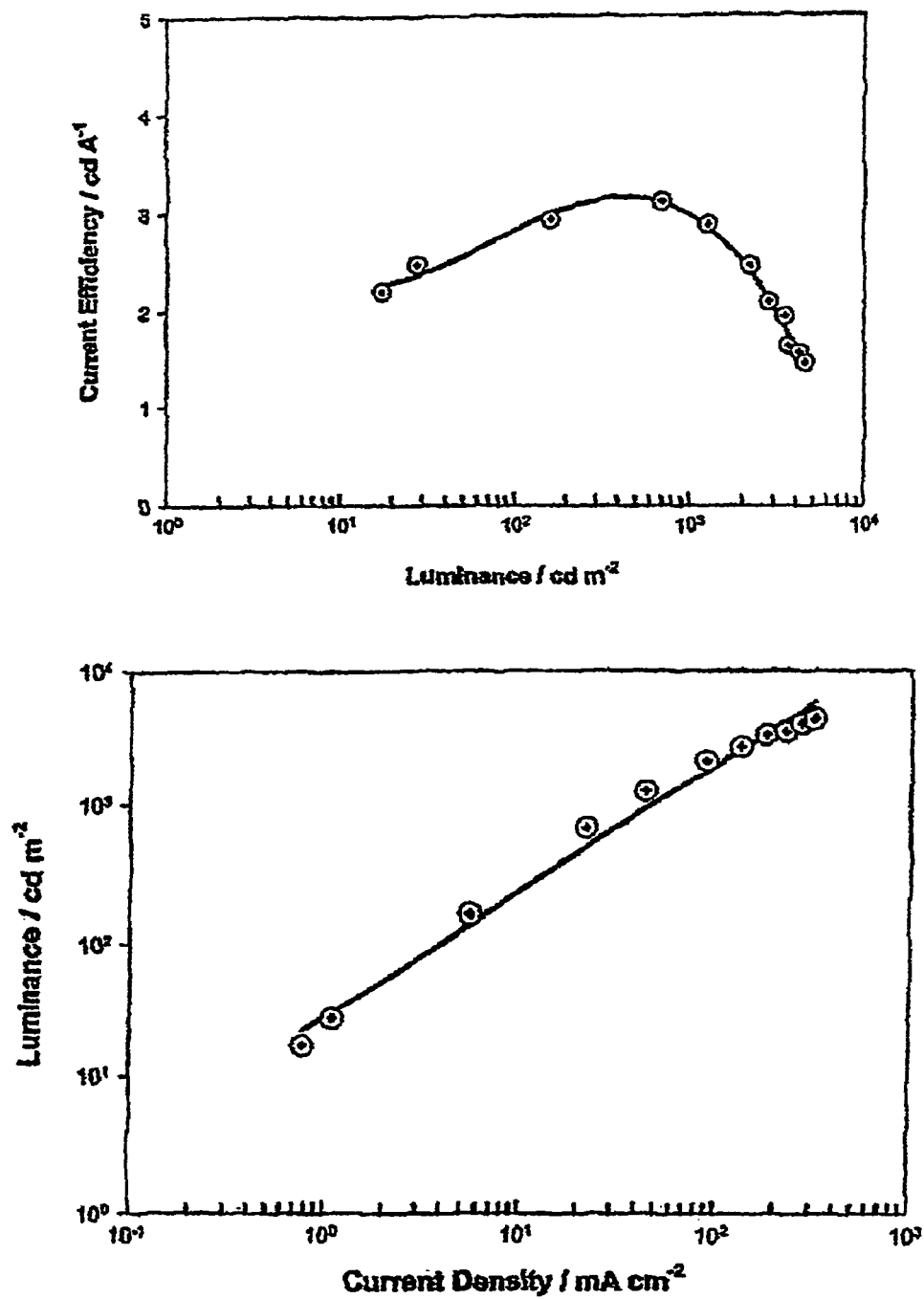
FIGS. 13 and 14 illustrate the electroluminescent properties of an electroluminescent device according to the present invention fabricated in accordance with Example 4.
Figure 14:
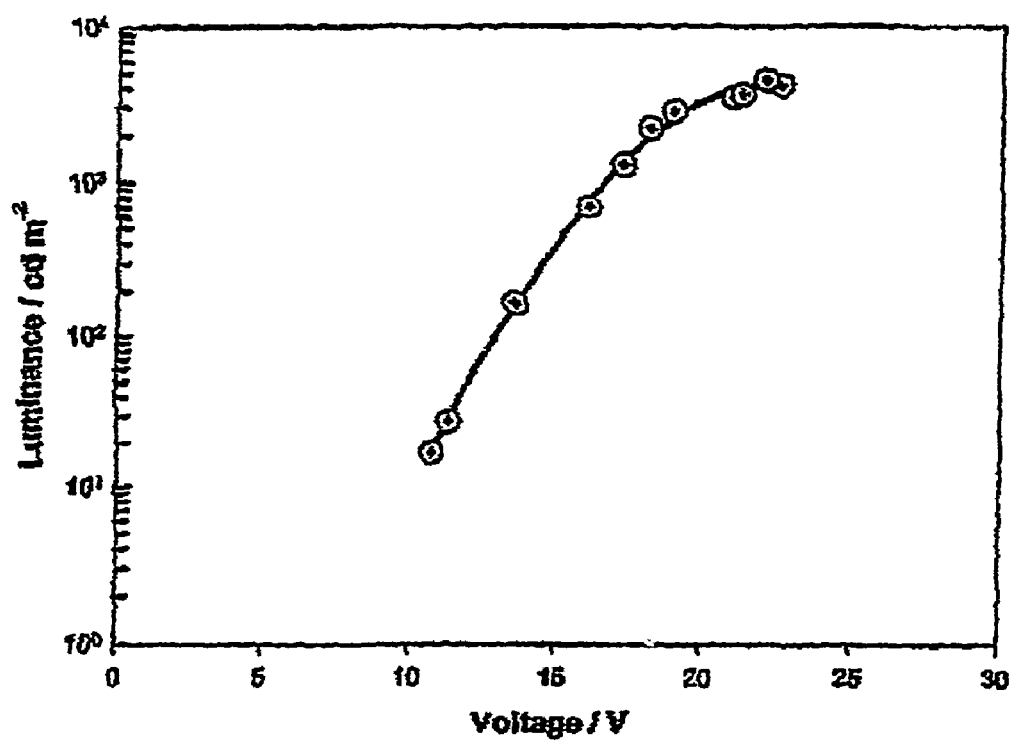

A device was made as in Example 2 except that it had the structure:
(1) ITO (100 nm)/(2) CuPc (10 nm)/(3) α-NPB (60 nM)/(4) Al(dbm)$_3$:Compound X (30:2 nm)/(5) BCP (6 nm)/(6) Zrq$_4$ (30 nm)/(7) LiF (0.5 nM)/Al Where Al(dbm)$_3$ is aluminium dibenzoyl methane. The electroluminescent properties were measured and the results are shown in FIGS. 13 and 14. The electroluminescent device on which FIGS. 13 and 14 are based demonstrated CIE coordinates of x=0.63 and y=0.37 and produced a peak luminescent wave length of about 600 nm.

EXAMPLE 5

Device 4

Figure 16:
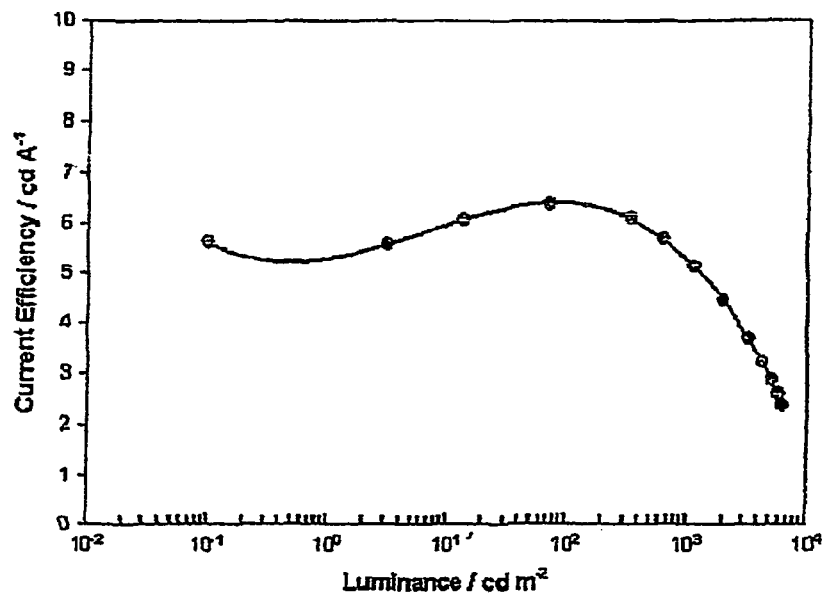
FIGS. 16 and 17 illustrate the electroluminescent properties of an electroluminescent device according to the present invention fabricated in accordance with Example 5.
Figure 16:
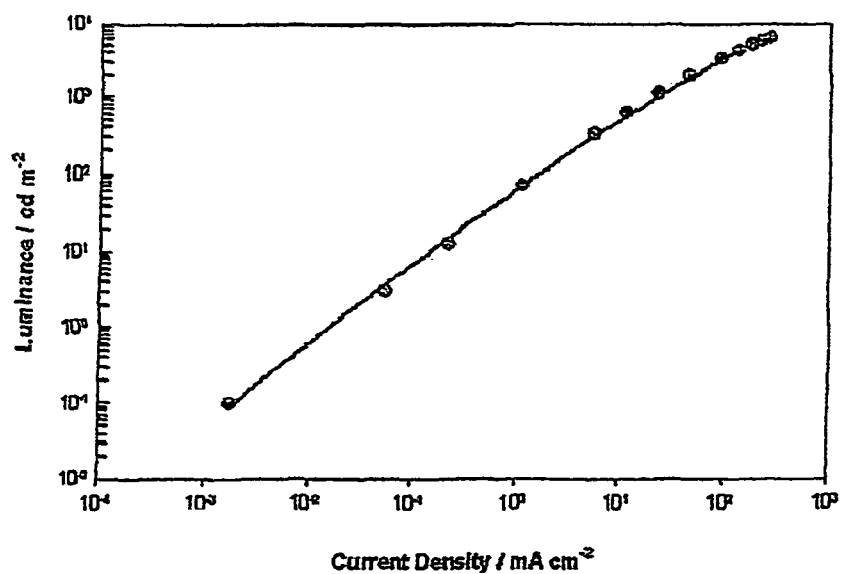
Figure 17:
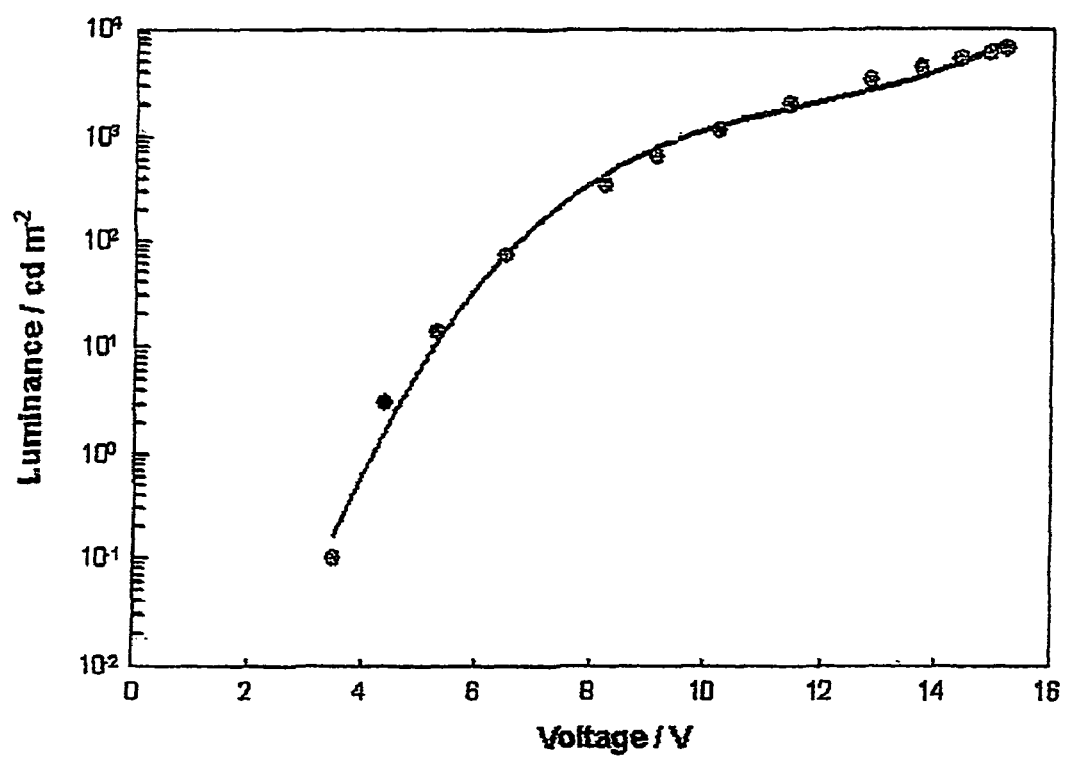

A device was made as in Example 2 except that it had the structure:
(1) ITO (110 nm)/(2) Complex A (10 nm)/(3) α-NPB (60 nm)/(4) CBP:Compound X (30:2 nm)/(5) Zrq$_4$(30 nm)/(6) LiF (0.5 nm)/Al Where Complex A is as in FIG. 15. The electroluminescent properties were measured and the results are shown in FIGS. 16 and 17.

EXAMPLE 6

Device 5

Figure 18:
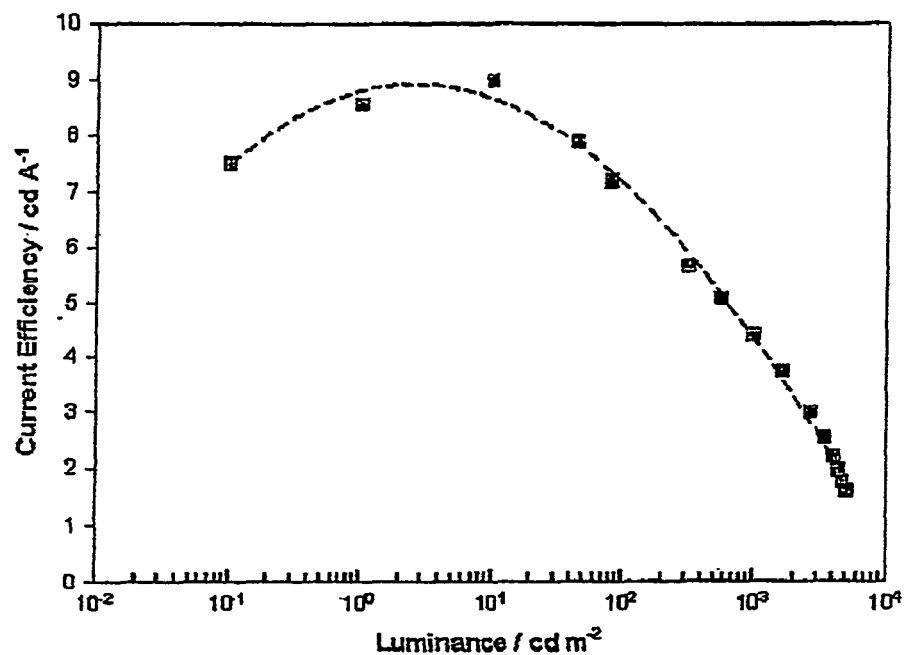
FIGS. 18 and 19 illustrate the electroluminescent properties of an electroluminescent device according to the present invention fabricated in accordance with Example 6.
Figure 18:
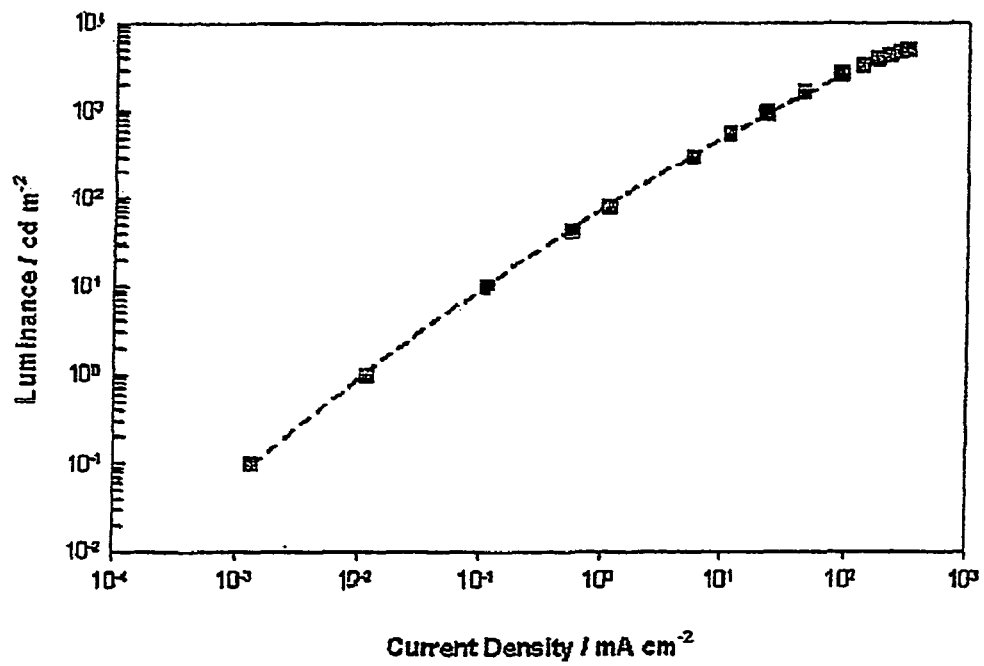
Figure 19:
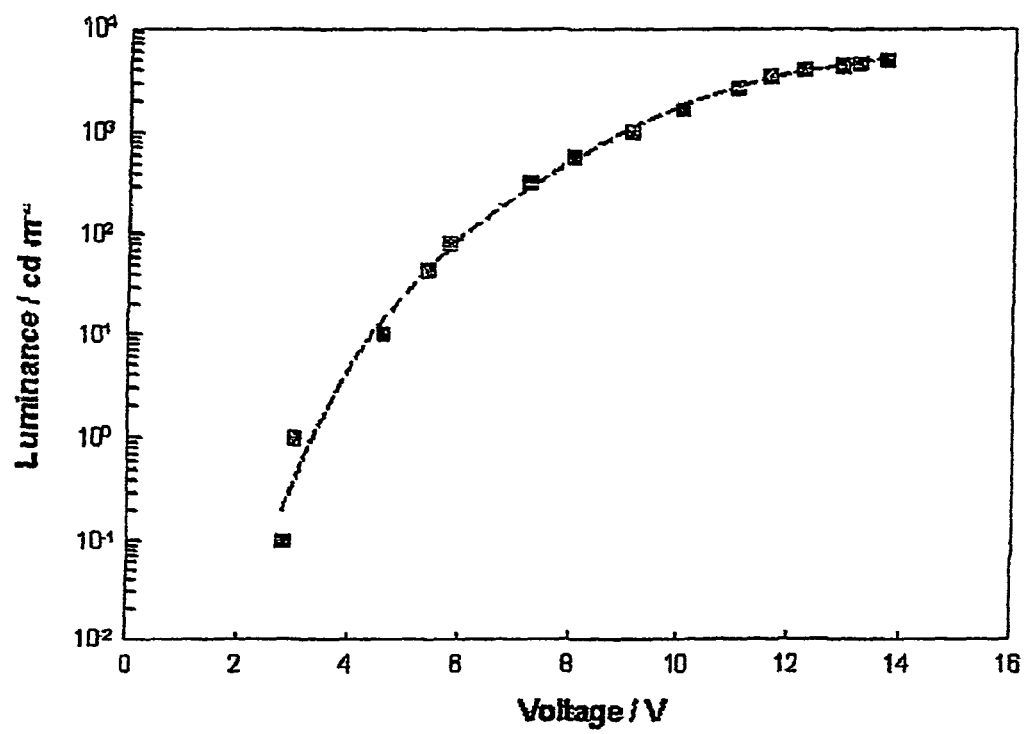

A device was made as in Example 2 except that it had the structure:
(1) ITO (110 nm)/(2) Complex A (10 nm)/(3) α-NPB (60 nm)/(4) BAlq$_2$:Compound X (30:2 nm)/(5) Zrq$_4$(30 nm)/(6) LiF (0.5 nm)/Al Where BAlq$_2$ is as in FIG. 15. The electroluminescent properties were measured and the results are shown in FIGS. 18 and 19.

EXAMPLE 7

Device 6

Figure 15:
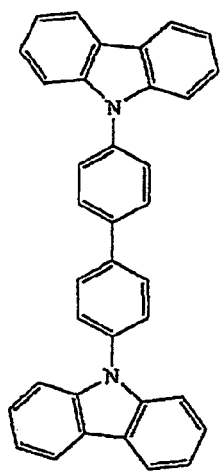
FIG. 15 illustrates chemical formulae of the materials CBP, BAlq$_2$, Complex A, Complex B and Zrq$_4$, as referenced in Examples 3, 5, 6 and 7.
Figure 15:
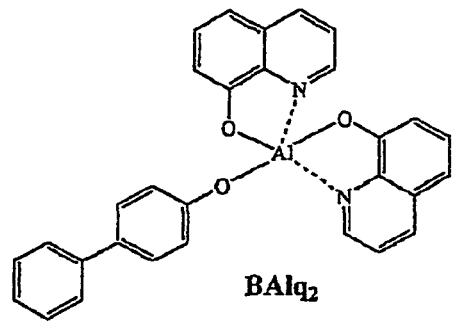
Figure 15:
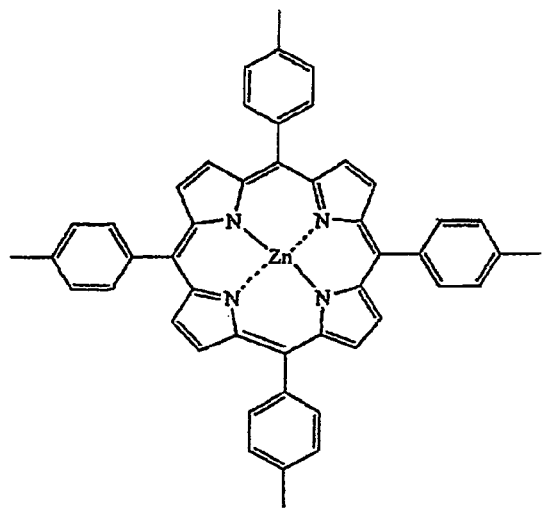
Figure 15:
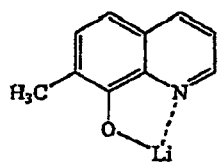
Figure 15:
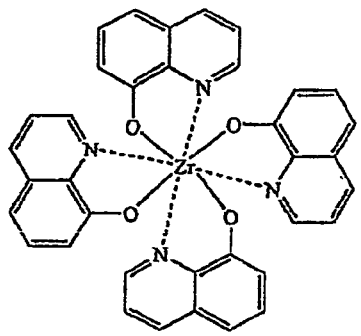
Figure 20:
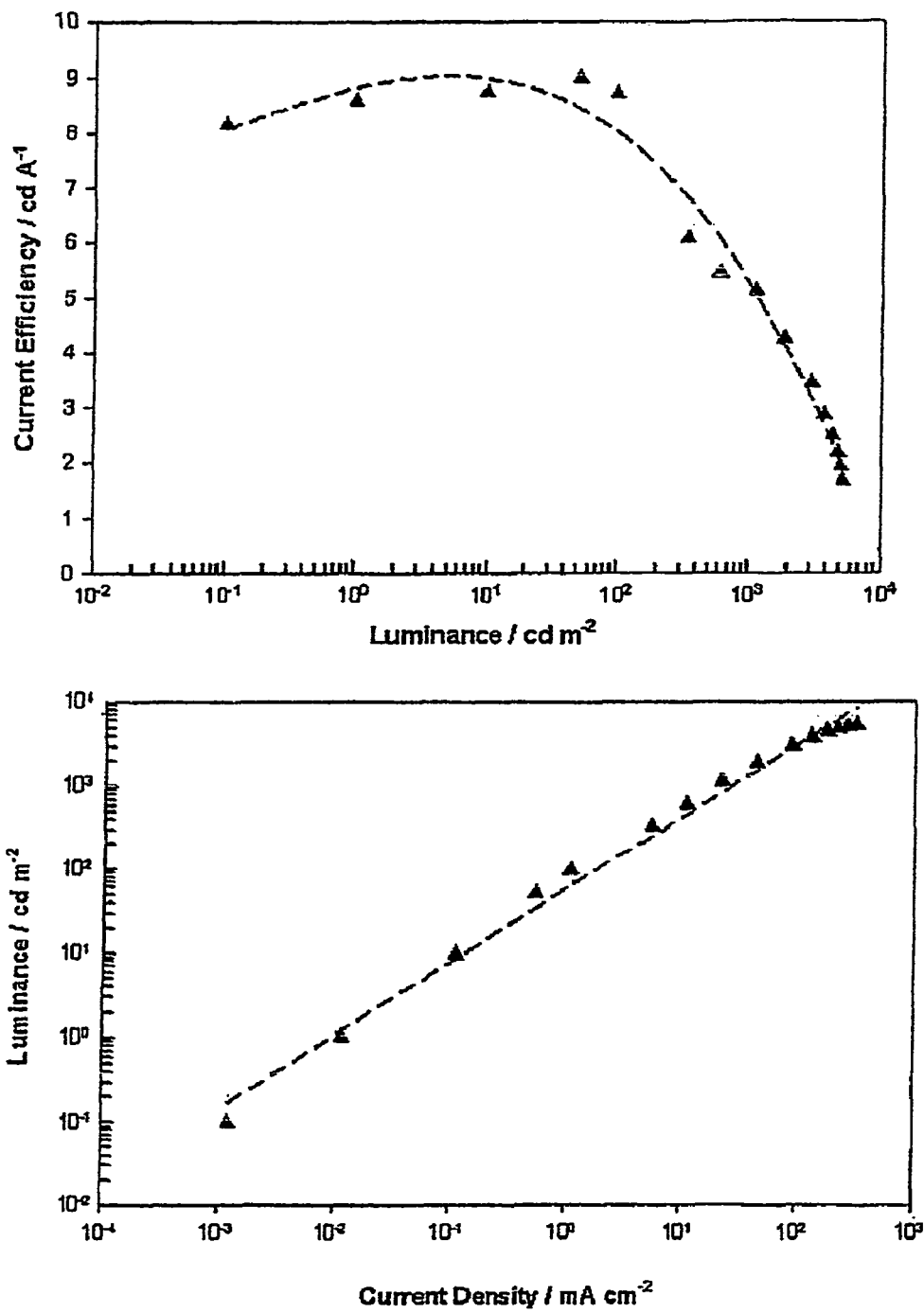
FIGS. 20 and 21 illustrate the electroluminescent properties of an electroluminescent device according to the present invention fabricated in accordance with Example 7.
Figure 21:
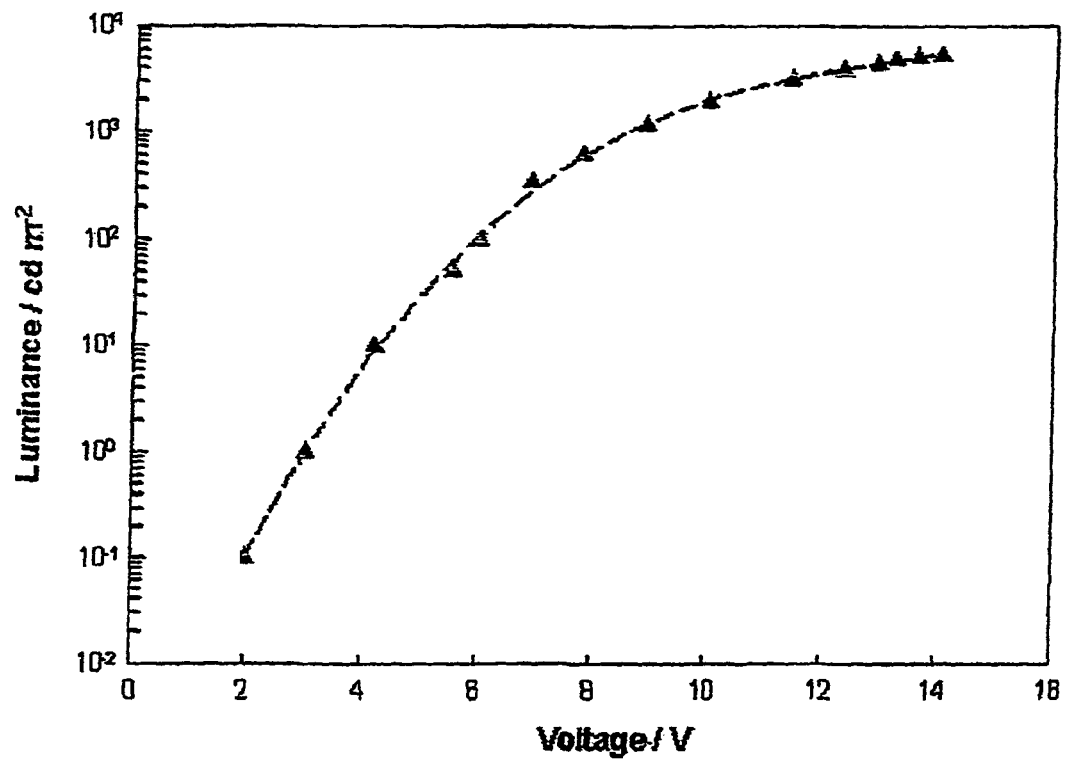

A device was made as in Example 2 except that it had the structure
(1) ITO (110 nm)/(2) Complex A (10 nm)/(3) α-NPB (60 nm)/(4) Complex B:Compound X (30:2 nm)(5) Zrq$_4$(30 nm)/(6) LiF (0.5 nm)/Al Where Complex B is as in FIG. 15. The electroluminescent properties were measured and the results are shown in FIGS. 20 and 21.

The invention claimed is:

1. An electroluminescent chemical complex represented by the general chemical formula:

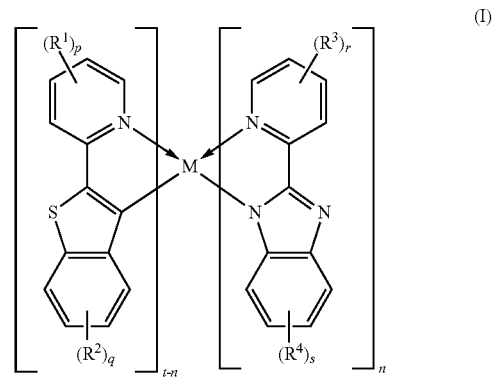

(I)

wherein:
(A) the letters M, t and n represent one of the following combinations:
(i) M is selected from the group consisting of ruthenium, rhodium, and iridium; t is 3; and n is 1 or 2;
(ii) M is selected from the group consisting of palladium or platinum; t is 2; and n is 1;
(iii) M is osmium; t is 3; and n is 1 or 2; and,
(iv) M is osmium; t is 4; and n is 1, 2 or 3;

(B) R₁, R₂, R₃ and R₄ can be the same or different and are independently selected from the group consisting of:
substituted and unsubstituted hydrocarbyl groups;
substituted and unsubstituted monocyclic and polycyclic heterocyclic groups;
substituted and unsubstituted hydrocarbyloxy or carboxy groups;
fluorocarbyl groups;
halogen;
nitrile;
amino;
alkylamino;
dialkylamino;
arylamino;
diarylamino; and
thiophenyl; and,
(C) p, q, r and s are independently selected from the integers 0, 1, 2 or 3;
subject to the proviso that, where any one of p, q, r and s is 2 or 3, only one of the R₁, R₂, R₃ and R₄ entities can be an entity other than saturated hydrocarbyl or halogen.

2. The complex of claim 1, wherein M is iridium.

3. The complex of claim 1, wherein n is 1 and t is 3.

4. The complex of claim 1, wherein at least one of R₁, R₂, R₃ and R₄ is a substituted or unsubstituted aliphatic or cycloaliphatic group and also wherein at least one of p, q, r and s is 1, 2 or 3.

5. The complex of claim 1, wherein at least one of R₁, R₂, R₃ and R₄ is alkyl or alkoxy and also wherein at least one of p, q, r and s is 1, 2 or 3.

6. The complex of claim 1, wherein at least one of R₁, R₂, R₃ and R₄ is methyl, ethyl, n-propyl, i-propyl, s-butyl, t-butyl, cyclohexyl, methoxy or ethoxy and also wherein at least one of p, q, r and s is 1, 2 or 3.

7. The complex of claim 1, wherein at least one of R₁, R₂, R₃ and R₄ is a substituted or unsubstituted monocyclic or polycyclic aromatic, aryloxy or heterocyclic structure and also wherein at least one of p, q, r and s is 1, 2 or 3.

8. The complex of claim 1, wherein at least one of R₁, R₂, R₃ and R₄ is phenyl, tolyl, fluorophenyl, biphenyl, naphthyl, fluorenyl, anthracenyl, phenanthrenyl or carbazolyl and also wherein at least one of p, q, r and s is 1, 2 or 3.

9. The complex of claim 1, wherein at least one of R₁, R₂, R₃ and R₄ is fluoro, chloro, methylamino, dimethylamino, benzylamino or dibenzylamino and also wherein at least one of p, q, r and s is 1, 2 or 3.

10. The complex of claim 1, wherein M is iridium, n is 1, t is 3 and p, q, r and s are 0.

11. An electroluminescent device comprising: (i) a first electrode;
(ii) a second electrode; and, (iii) an electroluminescent layer of a complex according to claim 1 located between said first and second electrodes.

12. The device of claim 11, wherein a layer of a hole transmitting material is located between the first electrode and the electroluminescent layer.

13. The device of claim 12, wherein the hole transmitting material is an aromatic amine.

14. The device of claim 12, wherein the hole transmitting material is a polyaromatic amine.

15. The device of claim 12, wherein the hole transmitting material is a film of a material selected from the group consisting of: α-NPB; poly(vinylcarbazole); N,N'-diphenyl-N,N'-bis (3-methylphenyl)-1,1'-biphenyl-4,4'-diamine (TPD); polyaniline; substituted polyanilines; polythiophenes; substituted polythiophenes; polysilanes; and substituted polysilanes.

16. The device of claim 12, wherein the hole transmitting material is a copolymer of aniline.

17. The device of claim 12, wherein the hole transmitting material is a conjugated polymer.

18. The device of claim 17, wherein the conjugated polymer is selected from the group consisting of poly (p-phenylenevinylene) (PPV) and copolymers of PPV.

19. The device of claim 11, wherein the electroluminescent layer further comprises a hole transmitting material.

20. The device of claim 11, wherein one of said first and second electrodes is a cathode and further wherein a layer of an electron transmitting material is located between the cathode and the electroluminescent layer.

21. The device of claim 20, wherein the electron transmitting material is a metal quinolate.

22. The device of claim 21, wherein the metal quinolate is selected from the group consisting of aluminum quinolate, zirconium quinolate, and lithium quinolate.

23. The device of claim 20, wherein the electron transmitting material has the general chemical formula Ax(DBM)ₙ where Ax is a metal, DBM is dibenzoyl methane, and n is an integer equal to the valency of Ax.

24. The device of claim 20, wherein the electron transmitting material is 9,10-dicyanoanthracene.

25. The device of claim 11, wherein the electroluminescent layer further comprises an electron transmitting material.

26. The device of claim 11, wherein the first electrode is a transparent electrically conducting glass electrode.

27. The device of claim 11, wherein the second electrode comprises a material selected from the group consisting of: aluminum, barium, rare earth metals, transition metals, calcium, lithium, magnesium and alloys thereof, and silver/magnesium alloys.

28. The device of claim 11, wherein the second electrode comprises a material selected from the group consisting of metals having a metal fluoride layer formed thereon.

29. The device of claim 28, wherein the metal fluoride is selected from the group consisting of lithium fluoride, potassium fluoride, caesium fluoride, and rare earth fluorides.

30. An electroluminescent composition comprising a complex according to claim 1 together with an electron-transporting host material or a hole-transporting host material.

31. A composition according to claim 30 wherein the host material is present in an amount ranging from about 0.1-20 wt. %.

32. An electroluminescent compound represented by the general chemical formula:

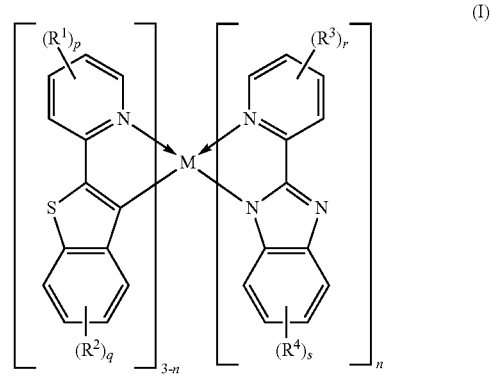

wherein:
M is selected from the group consisting of ruthenium, rhodium, osmium, and iridium;
n is 1 or 2;
$R_1$, $R_2$, $R_3$ and $R_4$ can be the same or different and are independently selected from the group consisting of:
substituted and unsubstituted hydrocarbyl groups;
substituted and unsubstituted monocyclic and polycyclic heterocyclic groups;
substituted and unsubstituted hydrocarbyloxy or carboxy groups;
fluorocarbyl groups;
halogen;
nitrile;
amino;
alkylamino;
dialkylamino;
arylamino;
diarylamino; and
thiophenyl; and,
p, q, r and s are independently selected from the integers 0, 1, 2 or 3;
subject to the proviso that, where any one of p, q, r and s is 2 or 3, only one of the $R_1$, $R_2$, $R_3$ and $R_4$ entities can be an entity other than saturated hydrocarbyl or halogen.

* * * * *